(12) United States Patent
Rhee et al.

(10) Patent No.: US 6,534,591 B2
(45) Date of Patent: *Mar. 18, 2003

(54) CROSS-LINKED POLYMER COMPOSITIONS AND METHODS FOR THEIR USE

(75) Inventors: Woonza M. Rhee, Palo Alto, CA (US); Frank A. DeLustro, Belmont, CA (US); Richard A. Berg, Los Altos, CA (US)

(73) Assignee: Cohesion Technologies, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/932,536

(22) Filed: Aug. 17, 2001

(65) Prior Publication Data

US 2002/0013408 A1 Jan. 31, 2002

Related U.S. Application Data

(63) Continuation of application No. 09/733,739, filed on Dec. 8, 2000, now Pat. No. 6,323,278, which is a continuation of application No. 09/302,852, filed on Apr. 30, 1999, now Pat. No. 6,166,130, which is a continuation of application No. 09/229,851, filed on Jan. 13, 1999, now Pat. No. 6,051,648, which is a continuation of application No. 08/769,806, filed on Dec. 18, 1996, now Pat. No. 5,874,500, which is a continuation-in-part of application No. 08/573,799, filed on Dec. 18, 1995, now abandoned.

(51) Int. Cl.$^7$ .................. C08F 283/00; C08G 63/91; C08G 69/48
(52) U.S. Cl. .................. 525/54.1; 525/419; 525/420; 525/425
(58) Field of Search ............... 525/54.1, 419, 525/420, 425

(56) References Cited

U.S. PATENT DOCUMENTS

| | | |
|---|---|---|
| 3,619,371 A | 11/1971 | Crook et al. |
| 3,742,955 A | 7/1973 | Battista et al. |
| 3,788,948 A | 1/1974 | Kegadal et al. |
| 3,810,473 A | 5/1974 | Cruz, Jr. et al. |
| 3,876,501 A | 4/1975 | Hanushewsky |
| 3,949,073 A | 4/1976 | Daniels et al. |
| 3,960,830 A | 6/1976 | Bayer et al. |
| 4,002,531 A | 1/1977 | Royer |
| 4,055,635 A | 10/1977 | Green et al. |
| 4,088,538 A | 5/1978 | Schneider |
| 4,101,380 A | 7/1978 | Rubinstein et al. |
| 4,164,559 A | 8/1979 | Miyata et al. |
| 4,179,337 A | 12/1979 | Davis et al. |
| 4,192,021 A | 3/1980 | Deibig et al. |
| 4,237,229 A | 12/1980 | Hartdegen et al. |
| 4,238,480 A | 12/1980 | Sawyer |
| 4,261,973 A | 4/1981 | Lee et al. |
| 4,279,812 A | 7/1981 | Cioca |
| 4,301,144 A | 11/1981 | Iwashita et al. |
| 4,314,380 A | 2/1982 | Miyata |
| 4,320,201 A | 3/1982 | Berg et al. |
| 4,357,274 A | 11/1982 | Werner |
| 4,390,519 A | 6/1983 | Sawyer |
| 4,404,970 A | 9/1983 | Sawyer |
| 4,412,947 A | 11/1983 | Cioca |
| 4,412,989 A | 11/1983 | Iwashita |
| 4,414,147 A | 11/1983 | Klibanov et al. |
| 4,415,628 A | 11/1983 | Cioca et al. |
| 4,415,665 A | 11/1983 | Mosbach et al. |
| 4,424,208 A | 1/1984 | Wallace et al. |
| 4,451,568 A | 5/1984 | Sneider et al. |
| 4,488,911 A | 12/1984 | Luck et al. |
| 4,495,285 A | 1/1985 | Shimizu et al. |
| 4,496,689 A | 1/1985 | Mitra |
| 4,515,637 A | 5/1985 | Cioca |
| 4,544,516 A | 10/1985 | Hughes et al. |
| 4,553,974 A | 11/1985 | Dewanjee |
| 4,557,764 A | 12/1985 | Chu |
| 4,563,350 A | 1/1986 | Nathan et al. |
| 4,563,351 A | 1/1986 | Nathan et al. |

(List continued on next page.)

FOREIGN PATENT DOCUMENTS

| | | |
|---|---|---|
| CA | 2134744 | 5/1995 |
| EP | 0013249 | 1/1980 |
| EP | 0042253 | 12/1981 |
| EP | 0154447 | 9/1985 |
| EP | 0157359 | 10/1985 |

(List continued on next page.)

OTHER PUBLICATIONS

Braatz et al. (1992), "A New Hydrophilic Polymer for Biomaterial Coatings with Low Protein Adsorption," *J. Biomater. Sci. Polymer Edn.* 3(6):451–462.

Poly(Eethylene Glycol) Chemistry: Biotechnical & Biomedical Applications, Chapter 22, J. Milton Harris, Ed., Plenum Press, NY (1992).

(List continued on next page.)

*Primary Examiner*—Nathan M. Nutter
(74) *Attorney, Agent, or Firm*—Dianne E. Reed; Reed & Eberle LLP

(57) ABSTRACT

Crosslinked polymer compositions comprise a first synthetic polymer containing multiple nucleophilic groups covalently bound to a second synthetic polymer containing multiple electrophilic groups. The first synthetic polymer is preferably a synthetic polypeptide or a polyethylene glycol that has been modified to contain multiple nucleophilic groups, such as primary amino (—$NH_2$) or thiol (—SH) groups. The second synthetic polymer may be a hydrophilic or hydrophobic synthetic polymer which contains, or has been derivatized to contain, two or more electrophilic groups, such as succinimidyl groups. The compositions may further comprise other components, such as naturally occurring polysaccharides or proteins (such as glycosaminoglycans or collagen) and/or biologically active agents. Also disclosed are methods for using the crosslinked polymer compositions to effect adhesion between a first surface and a second surface; to effect tissue augmentation; to prevent the formation of surgical adhesions; and to coat a surface of a synthetic implant.

30 Claims, 18 Drawing Sheets

U.S. PATENT DOCUMENTS

| | | |
|---|---|---|
| 4,563,490 A | 1/1986 | Stol et al. |
| 4,578,067 A | 3/1986 | Cruz, Jr. |
| 4,582,640 A | 4/1986 | Smestad et al. |
| 4,592,864 A | 6/1986 | Miyata et al. |
| 4,600,533 A | 7/1986 | Chu |
| 4,642,117 A | 2/1987 | Nguyen |
| 4,655,980 A | 4/1987 | Chu |
| 4,670,417 A | 6/1987 | Iwasaki et al. |
| 4,678,468 A | 7/1987 | Hiroyoshi |
| 4,687,820 A | 8/1987 | Hou et al. |
| 4,689,399 A | 8/1987 | Chu |
| 4,703,108 A | 10/1987 | Silver et al. |
| 4,704,131 A | 11/1987 | Noishiki et al. |
| 4,725,671 A | 2/1988 | Chu et al. |
| 4,732,863 A | 3/1988 | Tomasi |
| 4,737,544 A | 4/1988 | McCain et al. |
| 4,745,180 A | 5/1988 | Moreland et al. |
| 4,766,106 A | 8/1988 | Katre |
| 4,774,227 A | 9/1988 | Piez et al. |
| 4,789,663 A | 12/1988 | Wallace et al. |
| 4,795,467 A | 1/1989 | Piez et al. |
| 4,828,563 A | 5/1989 | Müller-Lierheim |
| 4,847,325 A | 7/1989 | Shadle et al. |
| 4,851,513 A | 7/1989 | Devore et al. |
| 4,886,866 A | 12/1989 | Braatz et al. |
| 4,935,465 A | 6/1990 | Garman |
| 4,950,483 A | 8/1990 | Ksander |
| 4,950,699 A | 8/1990 | Holman |
| 4,973,493 A | 11/1990 | Guire |
| 4,979,959 A | 12/1990 | Guire |
| 4,980,403 A | 12/1990 | Bateman et al. |
| 4,983,580 A | 1/1991 | Gibson |
| 5,024,742 A | 6/1991 | Nesburn et al. |
| 5,108,957 A | 4/1992 | Kelman et al. |
| 5,122,614 A | 6/1992 | Zalipsky |
| 5,141,747 A | 8/1992 | Scholz |
| 5,156,613 A | 10/1992 | Sawyer |
| 5,162,430 A | 11/1992 | Rhee et al. |
| 5,167,960 A | 12/1992 | Ito et al. |
| 5,169,754 A | 12/1992 | Siiman et al. |
| 5,192,316 A | 3/1993 | Ting |
| 5,198,493 A | 3/1993 | Holmberg et al. |
| 5,201,764 A | 4/1993 | Kelman et al. |
| 5,209,776 A | 5/1993 | Bass et al. |
| 5,219,564 A | 6/1993 | Zalipsky et al. |
| 5,219,895 A | 6/1993 | Kelman et al. |
| 5,264,214 A | 11/1993 | Rhee et al. |
| 5,290,552 A | 3/1994 | Sierra et al. |
| 5,292,802 A | 3/1994 | Rhee et al. |
| 5,298,643 A | 3/1994 | Greenwald |
| 5,304,595 A | 4/1994 | Rhee et al. |
| 5,306,500 A | 4/1994 | Rhee et al. |
| 5,308,889 A | 5/1994 | Rhee et al. |
| 5,321,095 A | 6/1994 | Greenwald |
| 5,324,775 A | 6/1994 | Rhee et al. |
| 5,324,844 A | 6/1994 | Zalipsky |
| 5,328,955 A | 7/1994 | Rhee et al. |
| 5,349,001 A | 9/1994 | Greenwald et al. |
| 5,354,336 A | 10/1994 | Kelman et al. |
| 5,364,622 A | 11/1994 | Franz et al. |
| 5,405,877 A | 4/1995 | Greenwald et al. |
| 5,410,016 A | 4/1995 | Hubbell et al. |
| 5,428,022 A | 6/1995 | Palefsky et al. |
| 5,455,027 A | 10/1995 | Zalipsky et al. |
| 5,475,052 A | 12/1995 | Rhee et al. |
| 5,510,418 A | 4/1996 | Rhee et al. |
| 5,514,379 A | 5/1996 | Weissleder et al. |
| 5,549,904 A | 8/1996 | Juergensen et al. |
| 5,565,519 A | 10/1996 | Rhee et al. |
| 5,567,422 A | 10/1996 | Greenwald |
| 5,580,923 A | 12/1996 | Yeung et al. |
| 5,605,976 A | 2/1997 | Martinez et al. |
| 5,612,460 A | 3/1997 | Zalipsky |
| 5,614,549 A | 3/1997 | Greenwald et al. |
| 5,614,587 A | 3/1997 | Rhee et al. |
| 5,626,863 A | 5/1997 | Hubbell et al. |
| 5,637,749 A | 6/1997 | Greenwald |
| 5,643,464 A | 7/1997 | Rhee et al. |
| 5,643,575 A | 7/1997 | Martinez et al. |
| 5,700,848 A | 12/1997 | Soon-Shiong et al. |
| 5,752,974 A | 5/1998 | Rhee et al. |
| 5,874,500 A | 2/1999 | Rhee et al. |
| 6,051,648 A * | 4/2000 | Rhee et al. .................. 525/419 |

FOREIGN PATENT DOCUMENTS

| | | |
|---|---|---|
| EP | 0171176 | 2/1986 |
| EP | 0243179 | 10/1987 |
| EP | 0330389 | 8/1989 |
| EP | 0341007 | 11/1989 |
| EP | 0431479 A1 | 6/1991 |
| EP | 0466383 | 1/1992 |
| EP | 0575273 | 12/1993 |
| EP | 0640647 | 3/1995 |
| EP | 0656214 | 6/1995 |
| EP | 0656215 | 6/1995 |
| EP | 0680990 | 11/1995 |
| EP | 0732109 | 9/1996 |
| FR | 2628634 | 9/1989 |
| GB | 1059455 | 2/1967 |
| JP | 4-227265 | 4/1990 |
| JP | 60-70972 | 3/1994 |
| JP | 07-090241 | 4/1995 |
| WO | WO 84/01106 | 3/1984 |
| WO | WO 85/04412 | 10/1985 |
| WO | WO 87/04078 | 7/1987 |
| WO | WO 90/05755 | 5/1990 |
| WO | WO 92/13025 | 8/1992 |
| WO | WO 92/13578 | 8/1992 |
| WO | WO 94/01483 | 1/1994 |
| WO | WO 94/03155 | 2/1994 |

OTHER PUBLICATIONS

Abuchowski et al. (1977), "Alteration of immunological properties of bovine serum albumin by covalent attachment of polyethylene glycol," *Biol. Chem.* 252(11):3578–3581.

Abuchowski et al. (1984), "Cancer therapy with chemically modified enzymes. I. Antitumor properties of polyethylene glycol–asparaginase conjugates," *Cancer Biochem. Biophys.* 7:175–186.

Abuchowski et al. (1977), "Effect of covalent attachment of polyethylene glycol on immunogenicity and circulating life of bovine liver catalase," *J. Biol. Chem.* 252(11):3582–3586.

Anderson et al. (1964), "The use of esters of n–hydroxysuccinimide in peptide synthesis," [???] 86:1839–1842.

Beauchamp et al. (1983), "A new procedure for the synthesis of polyethylene glycol–protein adducts: Effects on fuction, receptor recognition, and clearance of superoxide dismutase, lactoferrin, and $a_2$–macroglobulin," *Analytical Biochemistry* 131:25–33.

Bendich et al. (1982), "Immunological effects of native and polyethylene glycol–modified asparaginases from Vibro succinogenes and *Escherichia coli* in normal and tumor –bearing mice," *Clin. Exp. Immunol.* 48:273–278.

Chen et al. (1981), "Properties of two urate oxidase modified by the covalent attachment of poly(ethylene glycol)," *Biochem. Biophys. Acta.* 660:293–298.

Chvapil et al. (1969), "Some chemical and biological characteristics of a new collagen–polymer compound material," *J. Biomed. Mater. Res.* 3:315–332.

Davis et al. (1981), "Hypouricaemic effect of polyethyleneglycol modified urate oxidase," *Lancet* 22:281–283.

Doillon et al. (1986), *J. Biomed. Mat. Res.* 20(8):1219–1228.

Ferruti (1981), "Succinic half–esters of poly(ethylene glycol)s and their benzotriazole and imidazole derivatives as oligomeric drug–binding matrices," *Makromol. Chem.* 182:2183–2192.

Fleisher et al. (1987), "Regeneration of lost attachment apparatus in the dog using polygalactin–910," *J. Dent. Res.* 281(66 spec.), Abstract No. 1393.

Gander et al. (1988), "Crosslinked poly(alkylene oxides) for the preparation of controlled release micromatrices," *J. Controlled Release* 5:271–283.

Gnanou et al. (1984), "Hydrophilic polyurethane networks based on poly(ethylene oxide): Synthesis, characterization, and properties. Potential applications as biomaterials," *Macromolecules* 17:945–952.

Gomel et al. (1992), "Infertility surgery: Microsurgery," *Current Opinion in Obstetrics and Gynecology* 4:390–399.

Inada et al. (1984), "Ester synthesis catalyzed by polyethylene glycol–modified lipase in benzene," *Biochem. & Biophys. Res. Comm.* 122:845–850.

Katre et al. (1987), "Chemical modification of recombinant interleukin 2 by polyethylene glycol increases its potency in the murine meth A sarcoma model," *Proc. Natl. Acad. Sci. USA* 84:1487–1491.

McPherson et al. (1988), *Collagen and Related Research Clinical and Experimental* 8(1):83–100.

Nathan et al. (1993), "Copolymers of lysine and polyethylene glycol: A new family of functionalized drug carriers," *Bioconjugate Chem.* 4:54–62.

Nishida et al. (1984), "Hypouricaemic effect after oral administration in chickens of polyethylene glycol–modified uricase entrapped in liposomes," *J. Pharm. Pharmacol.* 36:354–355.

Pados et al. (1992), "Adhesions," *Current Opinion in Obstetrics and Gynecology* 4:421–428.

Pagidas et al. (1992), "Effects of ringer's lactate, interceed (TC7) and gore–tex surgical membrane on postsurgical adhesion formation," *Fertility and Sterility* 57(1):199–201.

Pyatak et al. (1980), "Preparation of a polyethylene glycol-:superoxide dismutase adduct, and an examination of its blood circulating life and anti–inflammatory activity," *Res. Com. Chem. Path. Pharmacol.* 29:113–127.

Ramshaw et al. (1984), "Precipitation of collagens by polyethylene glycols," *Anal. Biochem.* 141:361–365.

Savoca et al. (1979), "Preparation of a non–immunigenic arginase by the covalent attachment of polyethylene glycol," *Biochem. Biophys. Acta.* 578:47–53 (1979).

Sawhney et al. (1994), "Optimization of photopolymerized bioerodible hydrogel properties for adhesion prevention," *J. Biomed. Mat. Res.* 28:831–838.

Sperinde et al. (1997), "Phase transformation poly(ethylene glycol) hydrogels for tissue engineering and cell therapies," $23^{rd}$ *Annual Meeting of the Society for Biomaterials*, p. 247.

Steinleitner et al. (1991), "Poloxamer 407 as an intraperitoneal barrier material for the prevention of postsurgical adhesion formation and reformation in rodent models for reproductive surgery," *Obstetrics and Gynecology* 77:48–52.

Takahashi et al. (1984), "A chemical modification to make horseradish peroxidase soluble and active in benzene," *Biochem. & Biophys. Res. Comm.* 121:261–265.

Tulandi (1991), "Effects of fibrin sealant on tubal anastomosis and adhesion formation," *Fertility and Sterility* 56(1):136–138.

Ulbrich et al. (1986), "Poly(ethylene glycol)s containing enzymatically degradable bonds," *Makromol. Chem.* 187:1131–1144.

Urman et al. (1991), "Effect of hyaluronic acid on postoperative intraperitoneal adhesion formation and reformation in the rat model," *Fertility and Sterility* 56(3):568–570.

Viau et al. (1986), "Safety evaluation of free radical scavengers PEG–catalase and PEG–superoxide dismutase," *J. Free Rad. In Bio. & Med.* 2:283–288.

Viau et al. (1986), "Toxicologic studies of a conjugate of asparaginase and polyethylen glycol in mice, rats and dogs," *Am. J. Vet. Res.* 47:1398–1401.

West et al. (1995), "Comparison of covalently and physically cross–linked polyethylene glycol–based hydrogels for the prevention of postoperative adhesions in a rat model," *Biomaterials* 16:1153–1156.

Wieder et al. (1979), "Some properties of polyethylene glycol: Phenylalanine ammonia–lyase adducts," *J. Biol. Chem.* 254:12579–12587.

\* cited by examiner

Diamine

Triamine

CROSS-LINKED POLYMER COMPOSITIONS AND METHODS FOR THEIR USE

CROSS REFERENCES TO RELATED APPLICATION

This application is a continuation of U.S. application Ser. No. 09/733,739, filed Dec. 8, 2000 and issued as U.S. Pat. No. 6,323,278 on Nov. 27, 2001, which is a continuation of U.S. application Ser. No. 09/302,852, filed Apr. 30, 1999 and issued as U.S. Pat. No. 6,166,130 on Dec. 26, 2000, which was a continuation of U.S. application Ser. No. 09/229,851, filed Jan. 13, 1999 and issued as U.S. Pat. No. 6,051,648 On Apr. 18, 2000, which was a continuation of U.S. application Ser. No. 08/769,806, filed Dec. 18, 1996 and issued as U.S. Pat. No. 5,874,500 on Feb. 23, 1999, which was a continuation-in-part of U.S. application Ser. No. 08/573,799, filed Dec. 18, 1995, now abandoned, all of which applications are incorporated herein by reference in full, and to which we claim priority under 35 U.S.C. §120.

FIELD OF THE INVENTION

This invention relates generally to crosslinked polymer compositions comprising a first synthetic polymer containing multiple nucleophilic groups crosslinked using a second synthetic polymer containing multiple electrophilic groups, and to methods of using such compositions as bioadhesives, for tissue augmentation, in the prevention of surgical adhesions, and for coating surfaces of synthetic implants, as drug delivery matrices and for ophthalmic applications.

BACKGROUND OF THE INVENTION

U.S. Pat. No. 5,162,430, issued Nov. 10, 1992, to Rhee et al., and commonly owned by the assignee of the present invention, discloses collagen—synthetic polymer conjugates prepared by covalently binding collagen to synthetic hydrophilic polymers such as various derivatives of polyethylene glycol.

Commonly owned U.S. Pat. No. 5,324,775, issued Jun. 28, 1994, to Rhee et al., discloses various insert, naturally occurring, biocompatible polymers (such as polysaccharides) covalently bound to synthetic, non-immunogenic, hydrophilic polyethylene glycol polymers.

Commonly owned U.S. Pat. No. 5,328,955, issued Jul. 12, 1994, to Rhee et al., discloses various activated forms of polyethylene glycol and various linkages which can be used to produce collagen—synthetic polymer conjugates having a range of physical and chemical properties.

Commonly owned, copending U.S. application Ser. No. 08/403,358, filed Mar. 14, 1995, discloses a crosslinked biomaterial composition that is prepared using a hydrophobic crosslinking agent, or a mixture of hydrophilic and hydrophobic crosslinking agents. Preferred hydrophobic crosslinking agents include any hydrophobic polymer that contains, or can be chemically derivatized to contain, two or more succinimidyl groups.

Commonly owned, copending U.S. application Ser. No. 08/403,360, filed Mar. 14, 1995, discloses a composition useful in the prevention of surgical adhesions comprising a substrate material and an anti-adhesion binding agent, where the substrate material preferably comprises collagen and the binding agent preferably comprises at least one tissue-reactive functional group and at least one substrate-reactive functional group.

Commonly owned, U.S. application Ser. No. 08/476,825, filed Jun. 7, 1995, by Rhee et al., discloses bioadhesive compositions comprising collagen crosslinked using a multifunctionally activated synthetic hydrophilic polymer, as well as methods of using such compositions to effect adhesion between a first surface and a second surface, wherein at least one of the first and second surfaces is preferably a native tissue surface.

Japanese patent publication No. 07090241 discloses a composition used for temporary adhesion of a lens material to a support, to mount the material on a machining device, comprising a mixture of polyethylene glycol, having an average molecular weight in the range of 1000–5000, and poly-N-vinylpyrrolidone, having an average molecular weight in the range of 30,000–200,000.

West and Hubbell, *Biomaterials* (1995) 16:1153–1156, disclose the prevention of post-operative adhesions using a photopolymerized polyethylene glycol-co-lactic acid diacrylate hydrogel and a physically crosslinked polyethylene glycol-co-polypropylene glycol hydrogel, Poloxamer 407®.

Each publication cited above and herein is incorporated herein by reference in its entirety to describe and disclose the subject matter for which it is cited.

We now disclose a detailed description of preferred embodiments of the present invention, including crosslinked polymer compositions comprising synthetic polymers which contain multiple nucleophilic groups crosslinked using synthetic polymers containing multiple electrophilic groups, and methods for using these compositions to effect adhesion between a first surface and a second surface (wherein at least one of the first and second surfaces is preferably a native tissue surface) or to effect the augmentation of tissue, or to prevent surgical adhesion, or to coat surfaces of synthetic implants, or for delivering drugs or other active agents, or for ophthalmic applications.

SUMMARY OF THE INVENTION

The present invention discloses a crosslinked polymer composition comprising a first synthetic polymer containing two or more nucleophilic groups, and a second synthetic polymer containing two or more electrophilic groups which are capable of covalently bonding to one another to form a three dimensional matrix.

A preferred composition of the invention comprises polyethylene glycol containing two or more primary amino groups as the first synthetic polymer, and polyethylene glycol containing two or more succinimidyl groups (a five-membered ring structure represented herein as —N(COCH$_2$)$_2$) as the second synthetic polymer.

In a general method for preparing a composition for the delivery of a negatively charged compound (such as a protein or drug), a first synthetic polymer containing two or more nucleophilic groups is reacted with a second synthetic polymer containing two or more electrophilic groups, wherein the first synthetic polymer is present in molar excess in comparison to the second synthetic polymer, to form a positively charged matrix, which is then reacted with a negatively charged compound. In a general method for preparing a matrix for the delivery of a positively charged compound, a first synthetic polymer containing two or more nucleophilic groups is reacted with a second synthetic polymer containing two or more electrophilic groups, wherein the second synthetic polymer is present in molar excess in comparison to the first synthetic polymer, to form a negatively charged matrix, which is then reacted with a positively charged compound.

In a general method for effecting the nonsurgical attachment of a first surface to a second surface, a first synthetic polymer containing two or more nucleophilic groups is mixed with a second synthetic polymer containing two or more electrophilic groups to provide a reaction mixture; the reaction mixture is applied to a first surface before substantial crosslinking has occurred; and the first surface is contacted with a second surface to effect adhesion between the two surfaces.

In a general method for augmenting soft or hard tissue within the body of a mammalian subject, a first synthetic polymer containing two or more nucleophilic groups and a second synthetic polymer containing two or more electrophilic groups are administered simultaneously to a tissue site in need of augmentation and the reaction mixture is allowed to crosslink in situ to effect augmentation of the tissue. Alternatively, the first synthetic polymer and the second synthetic polymer may be mixed immediately prior to being administered to a tissue site, such that the majority of the crosslinking reaction proceeds in vivo.

In a general method for preventing the formation of adhesions following surgery, a first synthetic polymer containing two or more nucleophilic groups is mixed with a second synthetic polymer containing two or more electrophilic groups to provide a reaction mixture; the reaction mixture is applied to tissue comprising, surrounding, or adjacent to a surgical site before substantial crosslinking has occurred between the nucleophilic groups and the electrophilic groups; the reaction mixture is allowed to continue crosslinking in situ until equilibrium crosslinking has been achieved; and the surgical site is closed by conventional methodologies.

In a general method for coating a surface of a synthetic implant, a first synthetic polymer containing two or more nucleophilic groups is mixed with a second synthetic polymer containing two or more electrophilic groups to provide a reaction mixture; the reaction mixture is applied to a surface of a synthetic implant; and the components of the reaction mixture are allowed to crosslink with each other on the surface of the implant.

A feature of the invention is that the crosslinked polymer compositions are optically clear, making the compositions and methods of the invention particularly suited for use in ophthalmic applications in which optical clarity is a requirement. Furthermore, the compositions of the invention are comprised of biocompatible, non-immunogenic components which leave no toxic, potentially inflammatory or immunogenic reaction products at the tissue site of administration.

Another feature of the invention is that the crosslinked polymer compositions have a high compression strength and high swellability, i.e., a composition that has been dried will swell to three times (or more) its dried size upon rehydration, and is more "elastic." Since these polymers are generally very hydrophilic, they are more easily injected, i.e., the crosslinked composition stays as a "cohesive mass" when injected through a fine gague (27–30 gague) needle.

Yet another feature of the invention is that nucleophilic groups on the first synthetic polymer may covalently bind to primary amino groups on lysine residues of collagen molecules at the tissue site of administration, in effect, "biologically anchoring" the composition to the host tissue.

One feature of the invention is that the components of the compositions are non-immunogenic and do not require a "skin test" prior to beginning treatment, as do currently available xenogeneic collagen compositions, such as those manufactured from bovine hides.

Another feature of the invention is that, unlike collagen, the compositions of the invention are not subject to enzymatic cleavage by matrix metalloproteinases, such as collagenase, and are therefore not readily degradable in vivo and, as such, are expected to have greater long-term persistence in vivo than prior art collagen compositions.

Still another feature is that, when the groups on each of the polymers utilized react to form an amide bond, the manufacturing of the compositions of the present invention can be highly controlled rendering more consistent quality of products.

DETAILED DESCRIPTION OF THE PREFERRED EMBODIMENTS OF THE INVENTION

Figure 1:
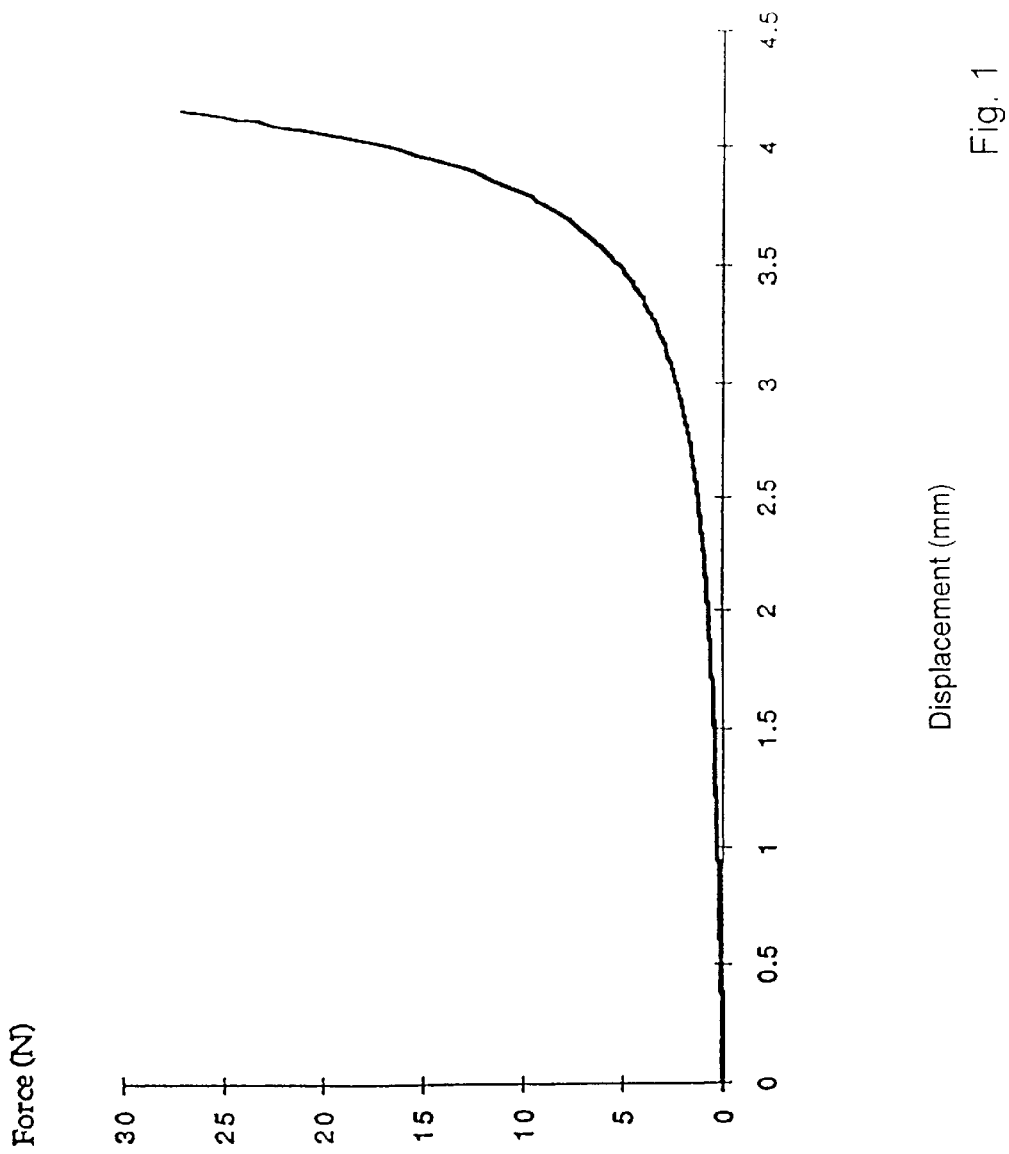
FIG. 1 shows compression force versus displacement for disks (approximate dimensions: 5 mm thick×5 mm diameter) of crosslinked polymer compositions comprising tetra-amino PEG (10,000 MW) crosslinked using tetrafunctionally activated SE-PEG (10,000 MW), measured using the Instron Universal Tester, Model 4202, at a compression rate of 2 mm per minute.

In accordance with the present invention, crosslinked polymer compositions are prepared by reacting a first synthetic polymer containing two or more nucleophilic groups with a second synthetic polymer containing two or more electrophilic groups capable of covalently binding with the nucleophilic groups on the first synthetic polymer.

The components of the present invention are non-immunogenic and, as such, do not require a "skin test" prior to starting treatment, as does xenogenic collagen. Also, unlike collagen, the compositions of the invention are not subject to enzymatic cleavage by matrix metalloproteinases (e.g., collagenase) and are therefore expected to have greater long-term persistence in vivo than currently available collagen compositions.

The concept behind the present invention is that a synthetic polymer containing multiple nucleophilic groups (represented below as "X") will react with a synthetic polymer containing multiple electrophilic groups (represented below as "Y"), resulting in a covalently bound polymer network, as follows:

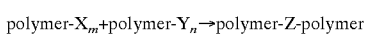

polymer-$X_m$+polymer-$Y_n$→polymer-Z-polymer wherein $m \geq 2$, $n \geq 2$, and $m+n \geq 5$;

X=—$NH_2$, —SH, —OH, —$PH_2$, —CO—NH—$NH_2$, etc., and can be the same or different;

Y=—$CO_2N(COCH_2)_2$, —$CO_2H$, —CHO, —$CHOCH_2$, —N=C=O, $SO_2CH$=$CH_2$, —$N(COCH)_2$), —S—S—($C_5H_4N$), etc., and can be the same or different; and Z=functional group resulting from the union of a nucleophilic group (X) and an electrophilic group (Y).

As noted above, it is also contemplated by the present invention that X and Y may be the same or different, i.e., the polymer may have two different electrophilic groups, or two different nucleophilic groups, such as with glutathione.

The backbone of each polymer is preferably an alkylene oxide, particularly, ethylene oxide, propylene oxide, and mixtures thereof Examples of difunctional alkylene oxides can be represented by:

wherein X and Y are as defined above, and the term "polymer" represents $-(CH_2CH_2O)_n-$ or $-(CH(CH_3)CH_2O)_n-$ or $-(CH_2CH_2O)_n-(CH(CH_3)CH_2O)-$.

The required functional group X or Y is commonly coupled to the polymer backbone by a linking group (represented below as "Q"), many of which are known or possible. There are many ways to prepare the various functionalized polymers, some of which are listed below:

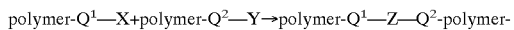

| wherein Q = | whole structure = |
|---|---|
| $-O-(CH_2)_n-$ | polymer-$O-(CH_2)_n-$X (or Y) |
| $-S-(CH_2)_n-$ | polymer-$S-(CH_2)_n-$X (or Y) |
| $-NH-(CH_2)_n-$ | polymer-$NH-(CH_2)_n-$X (or Y) |
| $-O_2C-NH-(CH_2)_n-$ | polymer-$O_2C-NH-(CH_2)_n-$X (or Y) |
| $-O_2C-(CH_2)_n-$ | polymer-$O_2C-(CH_2)_n-$X (or Y) |
| $-O_2C-CR^1H-$ | polymer-$O_2C-CRH-$X (or Y) |
| $-O-R^2-CO-NH-$ | polymer-$O-R-CO-NH-$X (or Y) | wherein n=1–10 in each case;

$R^1$=H, $CH_3$, $C_2H_5$, etc.;

$R^2=CH_2$, $CO-NH-CH_2CH_2$.

$Q^1$ and $Q^2$ may be the same or different.

For example, when $Q^2=OCH_2CH_2$ (there is no $Q^1$ in this case); Y=$-CO_2N(COCH_2)_2$; and X=$-NH_2$, $-SH$, or $-OH$, the resulting reactions and Z groups would be as follows:

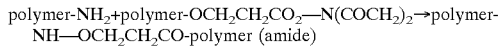

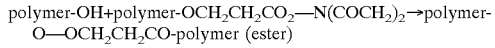

An additional group, represented below as "D", can be inserted between the polymer and the linking group to increase degradation of the crosslinked polymer composition in vivo, for example, for use in drug delivery applications.

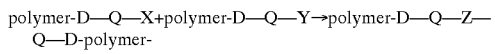

Some useful biodegradable groups "D" include lactide, glycolide, ε-caprolactone, poly(α-hydroxy acid), poly(amino acids), poly(anhydride), and various di- or tripeptides.

Synthetic Polymers

In order to prepare the compositions of the present invention, it is first necessary to provide a first synthetic polymer containing two or more nucleophilic groups, such as primary amino groups or thiol groups, and a second synthetic polymer containing two or more electrophilic groups capable of covalently binding with the nucleophilic groups on the second synthetic polymer.

As used herein, the term "polymer" refers inter alia to polyalkyls, polyamino acids and polysaccharides. Additionally, for external or oral use, the polymer may be polyacrylic acid or carbopol.

As used herein, the term "synthetic polymer" refers to polymers that are not naturally occurring and that are produced via chemical synthesis. As such, naturally occurring proteins such as collagen and naturally occurring polysaccharides such as hyaluronic acid are specifically excluded. Synthetic collagen, and synthetic hyaluronic acid, and their derivatives, are included. Synthetic polymers containing either nucleophilic or electrophilic groups are also referred to herein as "multifunctionally activated synthetic polymers". The term "multifunctionally activated" (or, simply, "activated") refers to synthetic polymers which have, or have been chemically modified to have, two or more nucleophilic or electrophilic groups which are capable of reacting with one another (i.e., the nucleophilic groups react with the electrophilic groups) to form covalent bonds. Types of multifunctionally activated synthetic polymers include difunctionally activated, tetrafunctionally activated, and star-branched polymers.

Multifunctionally activated synthetic polymers for use in the present invention must contain at least two, more preferably, at least three, functional groups in order to form a three-dimensional crosslinked network with synthetic polymers containing multiple nucleophilic groups (i.e., "multi-nucleophilic polymers"). In other words, they must be at least difunctionally activated, and are more preferably trifunctionally or tetrafunctionally activated. If the first synthetic polymer is a difunctionally activated synthetic polymer, the second synthetic polymer must contain three or more functional groups in order to obtain a three-dimensional crosslinked network. Most preferably, both the first and the second synthetic polymer contain at least three functional groups.

Synthetic Polymers Containing Multiple Nucleophilic Groups

Synthetic polymers containing multiple nucleophilic groups are also referred to generically herein as "multi-nucleophilic polymers". For use in the present invention, multi-nucleophilic polymers must contain at least two, more preferably, at least three, nucleophilic groups. If a synthetic polymer containing only two nucleophilic groups is used, a synthetic polymer containing three or more electrophilic groups must be used in order to obtain a three-dimensional crosslinked network.

Preferred multi-nucleophilic polymers for use in the compositions and methods of the present invention include synthetic polymers that contain, or have been modified to contain, multiple nucleophilic groups such as primary amino groups and thiol groups. Preferred multi-nucleophilic polymers include: (i) synthetic polypeptides that have been synthesized to contain two or more primary amino groups or thiol groups; and (ii) polyethylene glycols that have been modified to contain two or more primary amino groups or thiol groups. In general, reaction of a thiol group with an electrophilic group tends to proceed more slowly than reaction of a primary amino group with an electrophilic group.

Preferred multi-nucleophilic polypeptides are synthetic polypeptides that have been synthesized to incorporate amino acids containing primary amino groups (such as lysine) and/or amino acids containing thiol groups (such as cysteine). Poly(lysine), a synthetically produced polymer of the amino acid lysine (145 MW), is particularly preferred. Poly(lysine)s have been prepared having anywhere from 6 to about 4,000 primary amino groups, corresponding to molecular weights of about 870 to about 580,000.

Poly(lysine)s for use in the present invention preferably have a molecular weight within the range of about 1,000 to about 300,000; more preferably, within the range of about 5,000 to about 100,000; most preferably, within the range of about 8,000 to about 15,000. Poly(lysine)s of varying molecular weights are commercially available from Peninsula Laboratories, Inc. (Belmont, Calif.).

Polyethylene glycol can be chemically modified to contain multiple primary amino or thiol groups according to methods set forth, for example, in Chapter 22 of *Poly(ethylene Glycol) Chemistry: Biotechnical and Biomedical Applications*, J. Milton Harris, ed., Plenum Press, NY (1992). Polyethylene glycols which have been modified to contain two or more primary amino groups are referred to herein as "multi-amino PEGs". Polyethylene glycols which have been modified to contain two or more thiol groups are referred to herein as "multi-thiol PEGs". As used herein, the term "polyethylene glycol(s)" includes modified and or derivatized polyethylene glycol(s).

Figure 3A:
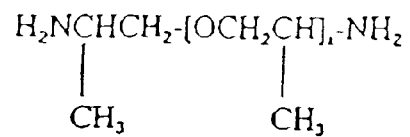
FIG. 3 shows the chemical structure of two commercially available polyethylene glycols containing multiple primary amino groups.
Figure 3B:
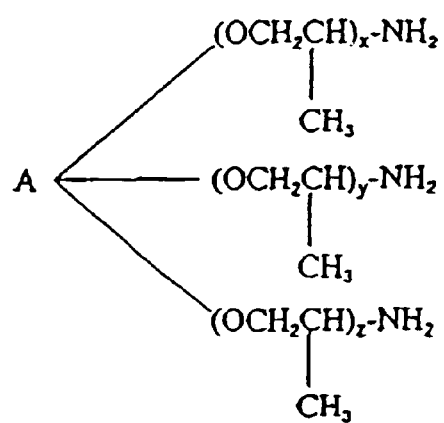

Various forms of multi-amino PEG are commercially available from Shearwater Polymers (Huntsville, Ala.) and from Texaco Chemical Company (Houston, Tex.) under the name "Jeffamine". Multi-amino PEGs useful in the present invention include Texaco's Jeffamine diamines ("D" series) and triamines ("T" series), which contain two and three primary amino groups per molecule, respectively. General structures for the Jeffamine diamines and triamines are shown in FIG. 3.

Polyamines such as ethylenediamine ($H_2N-CH_2CH_2-NH_2$), tetramethylenediamine ($H_2N-(CH_2)_4-NH_2$), pentamethylenediamine (cadaverine) ($H_2N-(CH_2)_5-NH_2$), hexamethylenediamine ($H_2N-(CH_2)_6-NH_2$), bis(2-hydroxyethyl)amine ($HN-(CH_2CH_2OH)_2$), bis(2)aminoethyl)amine ($HN-(CH_2CH_2NH_2)_2$), and tris(2-aminoethyl)amine ($N-(CH_2CH_2NH_2)_3$) may also be used as the synthetic polymer containing multiple nucleophilic groups.

Synthetic Polymers Containing Multiple Electrophilic Groups

Synthetic polymers containing multiple electrophilic groups are also referred to herein as "multi-electrophilic polymers." For use in the present invention, the multifunctionally activated synthetic polymers must contain at least two, more preferably, at least three, electrophilic groups in order to form a three-dimensional crosslinked network with multi-nucleophilic polymers Preferred multi-electrophilic polymers for use in the compositions of the invention are polymers which contain two or more succinimidyl groups capable of forming covalent bonds with electrophilic groups on other molecules. Succinimidyl groups are highly reactive with materials containing primary amino ($-NH_2$) groups, such as multi-amino PEG, poly(lysine), or collagen. Succinimidyl groups are slightly less reactive with materials containing thiol ($-SH$) groups, such as multi-thiol PEG or synthetic polypeptides containing multiple cysteine residues.

As used herein, the term "containing two or more succinimidyl groups" is meant to encompass polymers which are commercially available containing two or more succinimidyl groups, as well as those that must be chemically derivatized to contain two or more succinimidyl groups. As used herein, the term "succinimidyl group" is intended to encompass sulfosuccinimidyl groups and other such variations of the "generic" succinimidyl group. The presence of the sodium sulfite moiety on the sulfosuccinimidyl group serves to increase the solubility of the polymer.

Hydrophilic Polymers

Hydrophilic polymers and, in particular, various polyethylene glycols, are preferred for use in the compositions of the present invention. As used herein, the term "PEG" refers to polymers having the repeating structure $(OCH_2CH_2)_n$.

Structures for some specific, tetrafunctionally activated forms of PEG are shown in FIGS. 4 to 13, as are generalized reaction products obtained by reacting tetrafunctionally activated PEGs with multi-amino PEGS. As depicted in the Figures, the succinimidyl group is a five-member ring structure represented as $-N(COCH_2)_2$. In FIGS. 4 to 13, the symbol $\sim\sim\sim$ denotes an open linkage.

Figure 4:
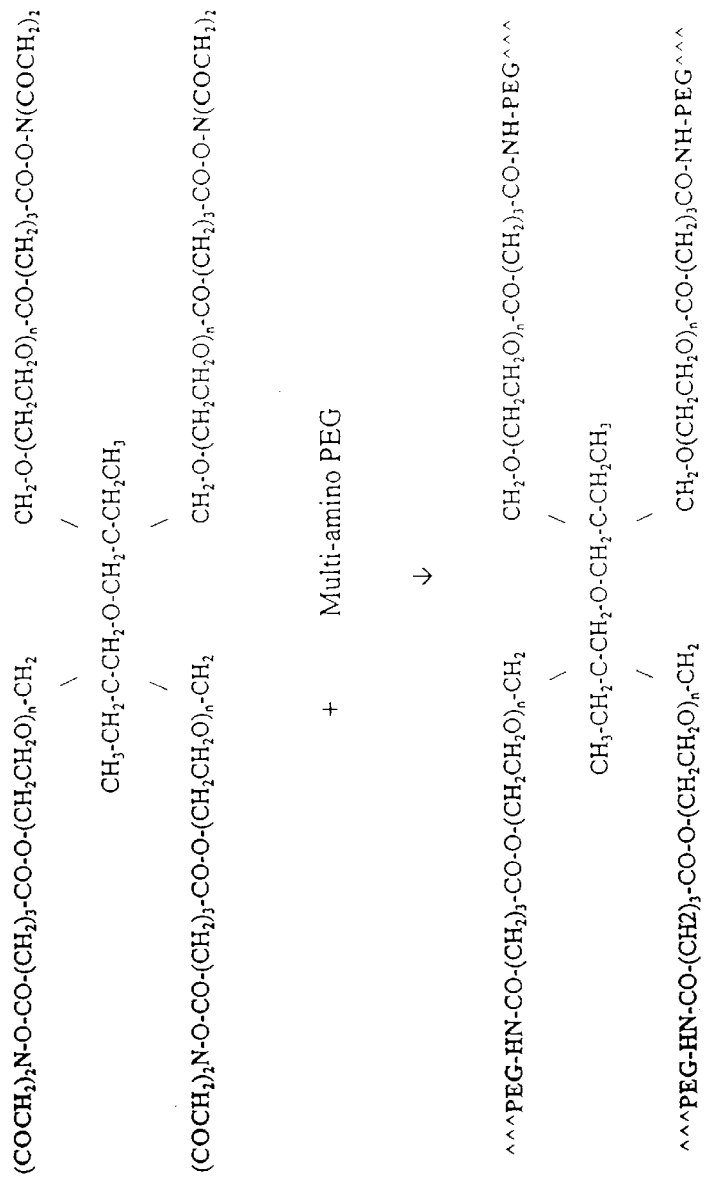
FIGS. 4 to 13 show the formation of various crosslinked synthetic polymer compositions from hydrophilic polymers.

FIG. 4 shows the reaction of tetrafunctionally activated PEG succinimidyl glutarate, referred to herein as SG-PEG, with multi-amino PEG, and the reaction product obtained thereby.

Figure 5:
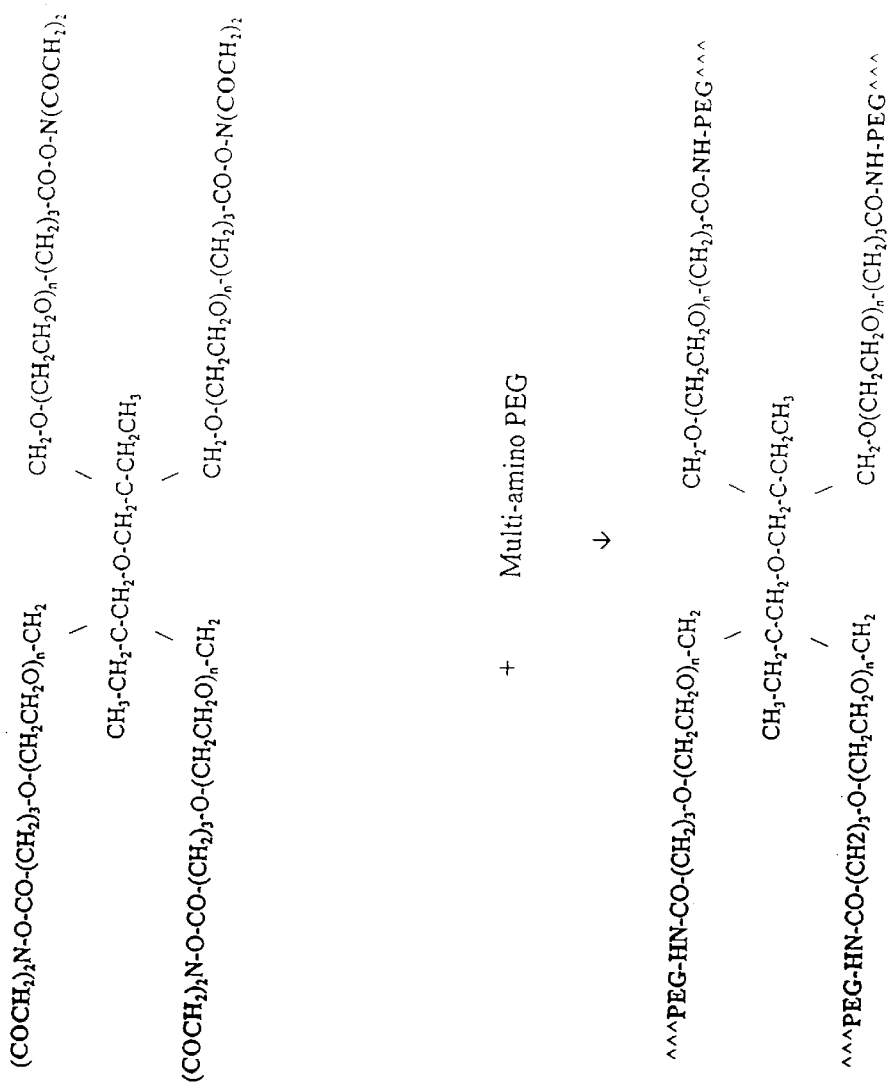

Another activated form of PEG is referred to as PEG succinimidyl propionate (SE-PEG). The structural formula for tetrafunctionally activated SE-PEG and the reaction product obtained by reacting it with multi-amino PEG are shown in FIG. 5. In a general structural formula for the compound, the subscript 3 is replaced with an "m". In the embodiment shown in FIG. 4, m=3, in that there are three repeating $CH_2$ groups on either side of the PEG.

The structure in FIG. 5 results in a conjugate which includes an "ether" linkage which is less subject to hydrolysis. This is distinct from the conjugate shown in FIG. 4, wherein an ester linkage is provided. The ester linkage is subject to hydrolysis under physiological conditions.

Figure 6:
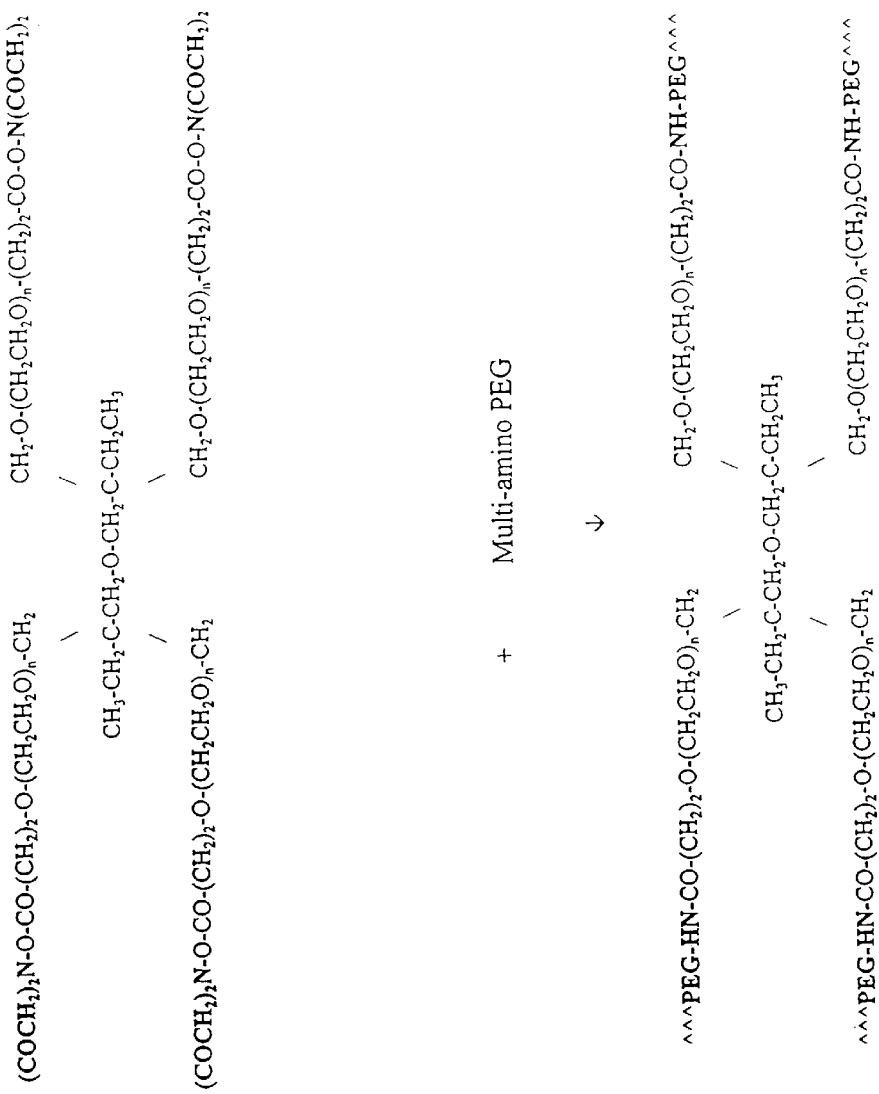

Yet another functionally activated form of polyethylene glycol, wherein m=2, is shown in FIG. 6, as is the conjugate formed by reacting the tetrafunctionally activated PEG with a multi-amino PEG.

Figure 7:
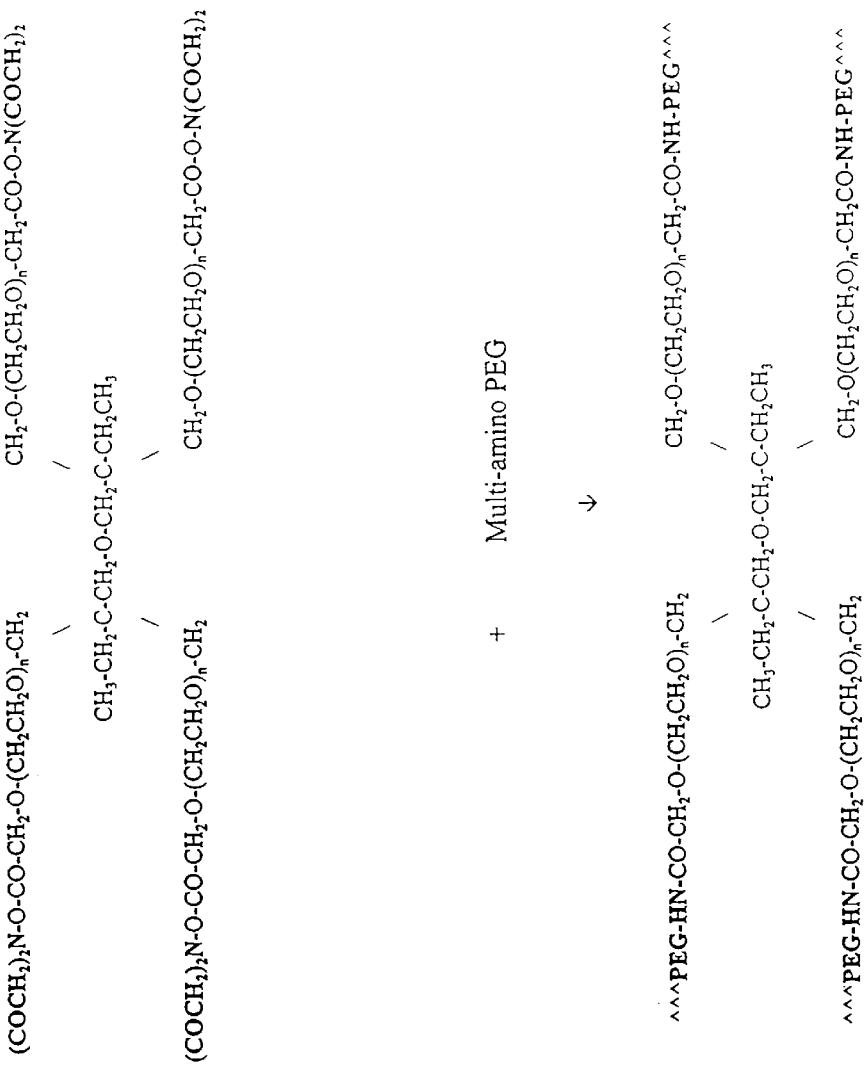

Another functionally activated PEG similar to the compounds of FIGS. 5 and 6 is provided when m=1. The structural formula of the tetrafunctionally activated PEG and resulting conjugate formed by reacting the activated PEG with multi-amino PEG are shown in FIG. 7. It is noted that this conjugate includes both an ether and a peptide linkage. These linkages are stable under physiological conditions.

Figure 8:
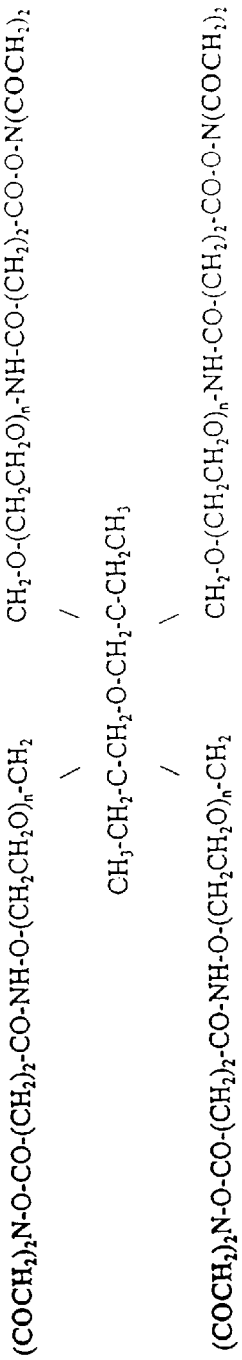
Figure 8:
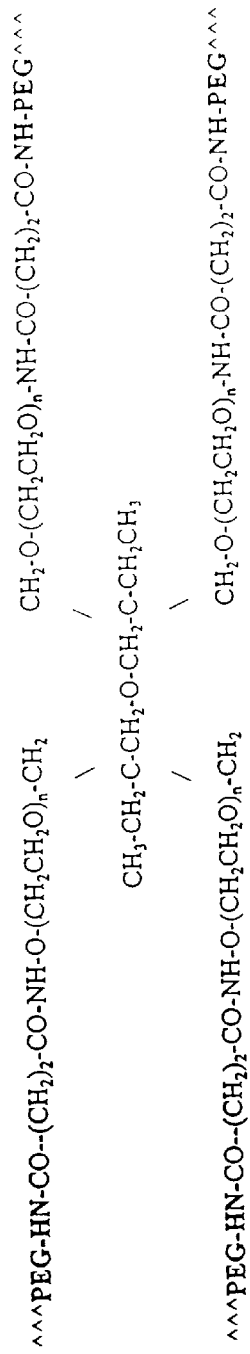

Another functionally activated form of PEG is referred to as PEG succinimidyl succinamide (SSA-PEG). The structural formula for the tetrafunctionally activated form of this compound and the reaction product obtained by reacting it with multi-amino PEG are shown in FIG. 8. In the structure shown in FIG. 8, m=2; however, related compounds, wherein m=1 or m=3–10, may also be used in the compositions of the invention.

The structure in FIG. 8 results in a conjugate which includes an "amide" linkage which, like the ether linkage previously described, is less subject to hydrolysis and is therefore more stable than an ester linkage.

Figure 9:
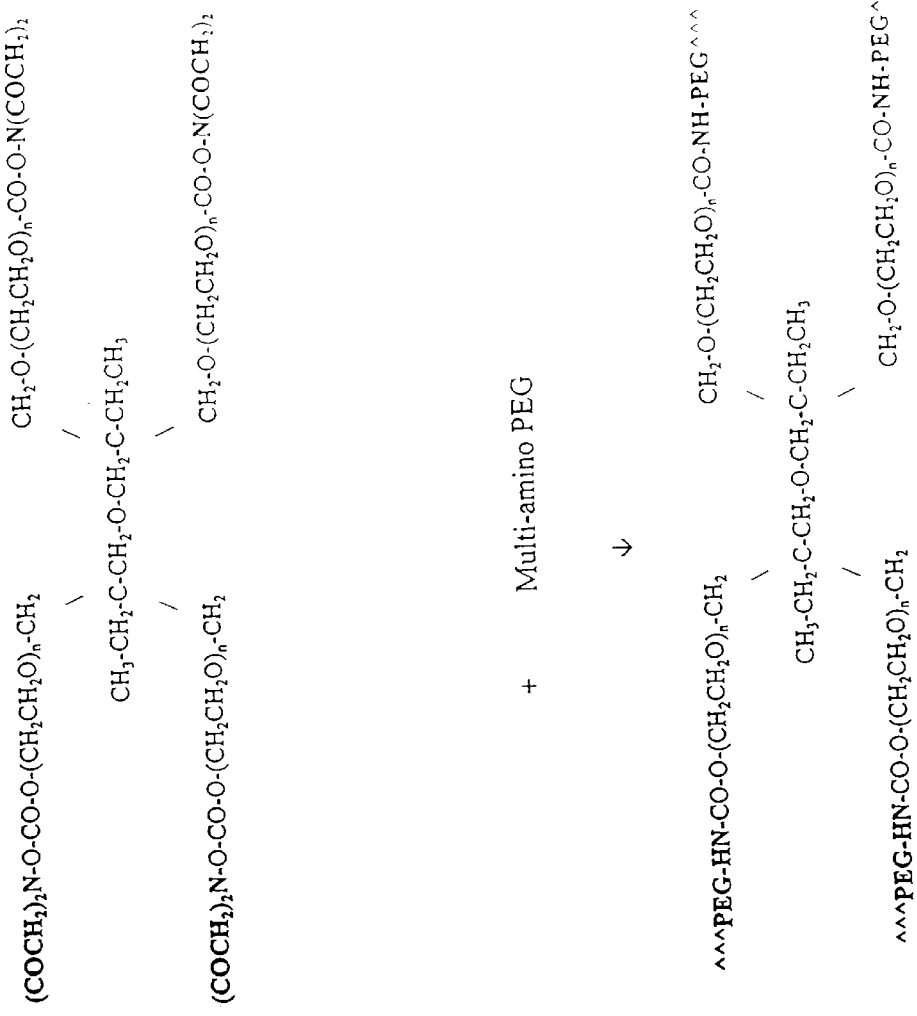

Yet another activated form of PEG is provided when m=0. This compound is referred to as PEG succinimidyl carbonate (SC-PEG). The structural formula of tetrafunctionally activated SC-PEG and the conjugate formed by reacting it with multi-amino PEG are shown in FIG. 9.

Figure 10:
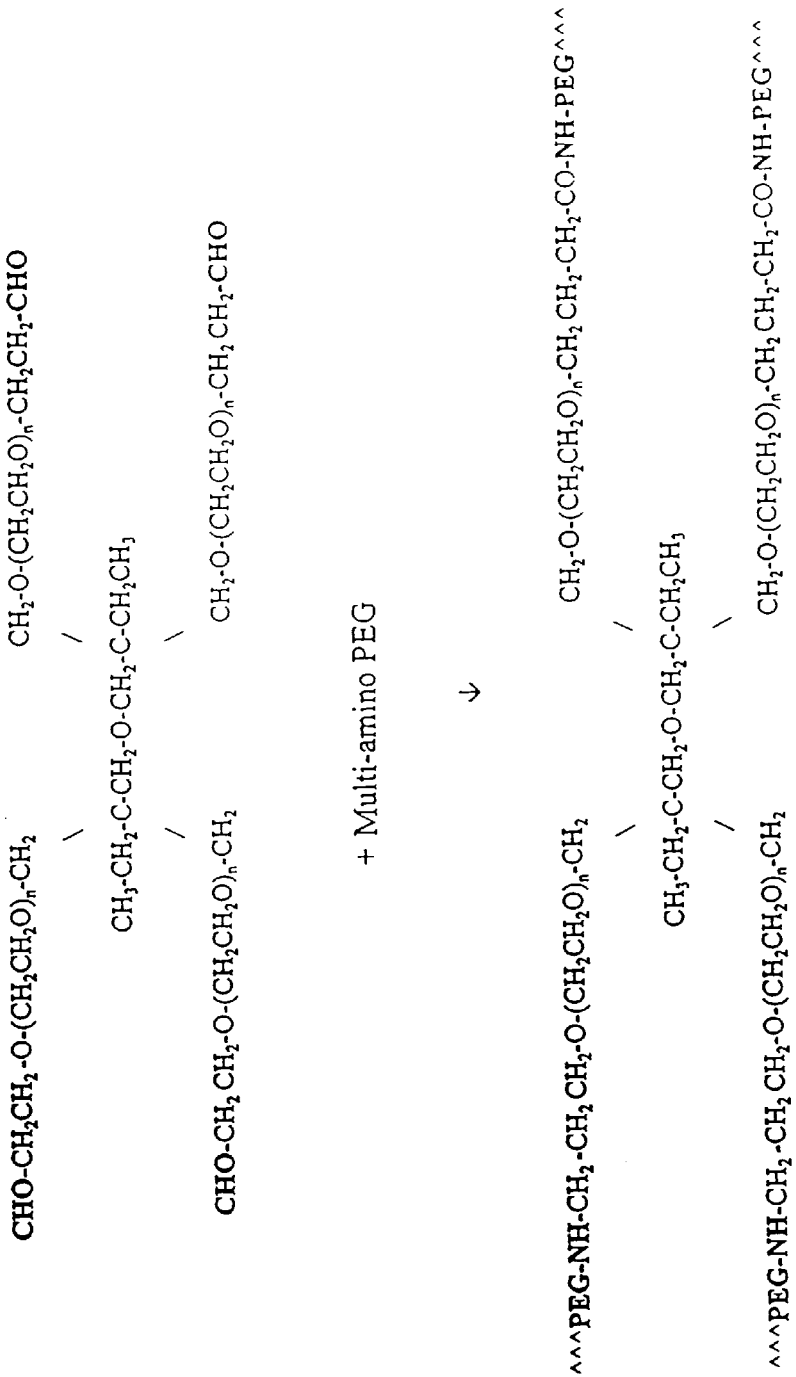

As discussed above, preferred activated polyethylene glycol derivatives for use in the invention contain succinimidyl groups as the reactive group. However, different activating groups can be attached at sites along the length of the PEG molecule. For example, PEG can be derivatized to form functionally activated PEG propion aldehyde (A-PEG), the tetrafunctionally activated form of which is shown in FIG. 10, as is the conjugate formed by the reaction of A-PEG with multi-amino PEG. The linkage shown in FIG. 10 is referred to as a —$(CH_2)_m$—NH—linkage, where m=1–10.

Figure 11:
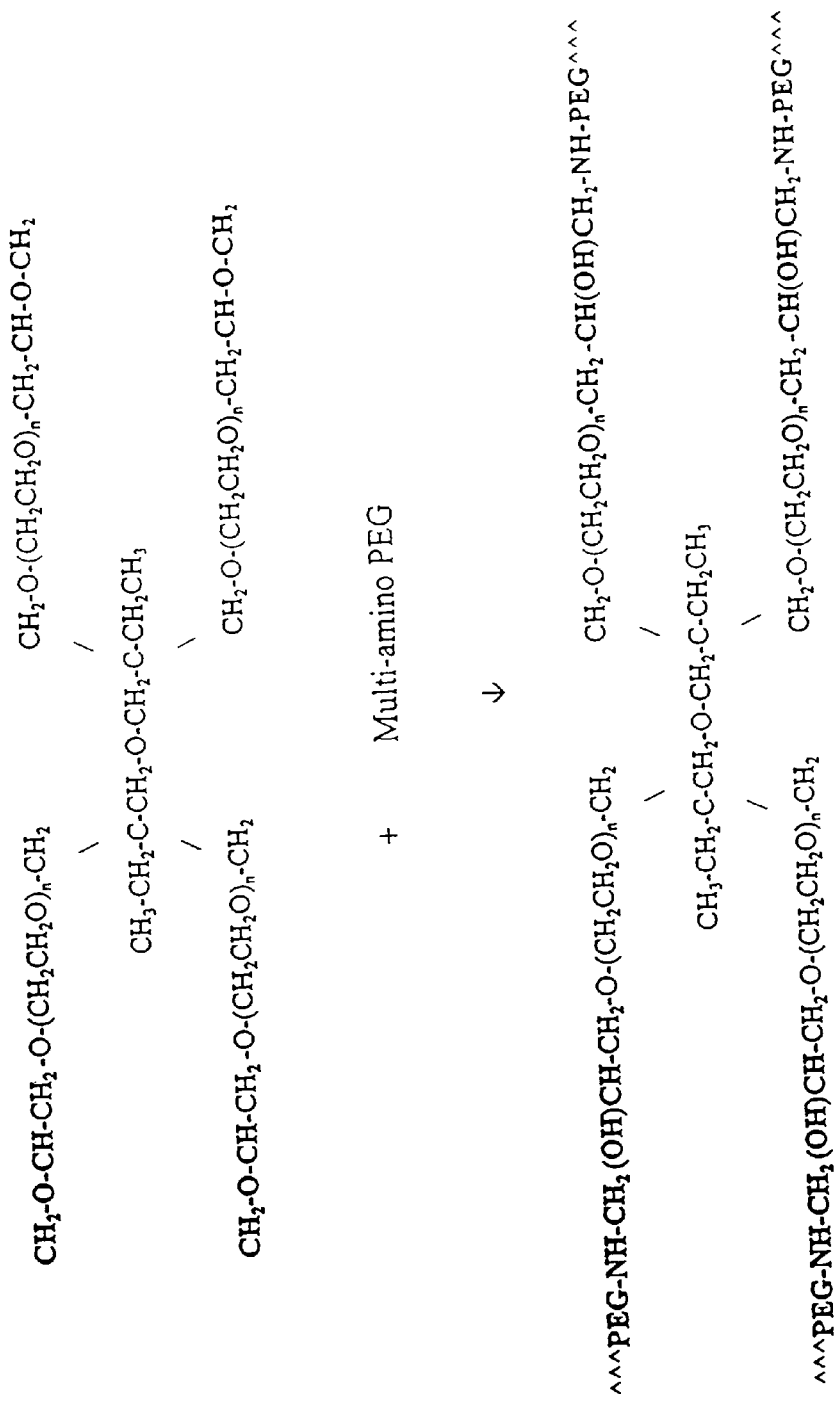

Yet another form of activated polyethylene glycol is functionally activated PEG glycidyl ether (E-PEG), of which the tetrafunctionally activated compound is shown in FIG. 11, as is the conjugate formed by reacting such with multi-amino PEG.

Figure 12:
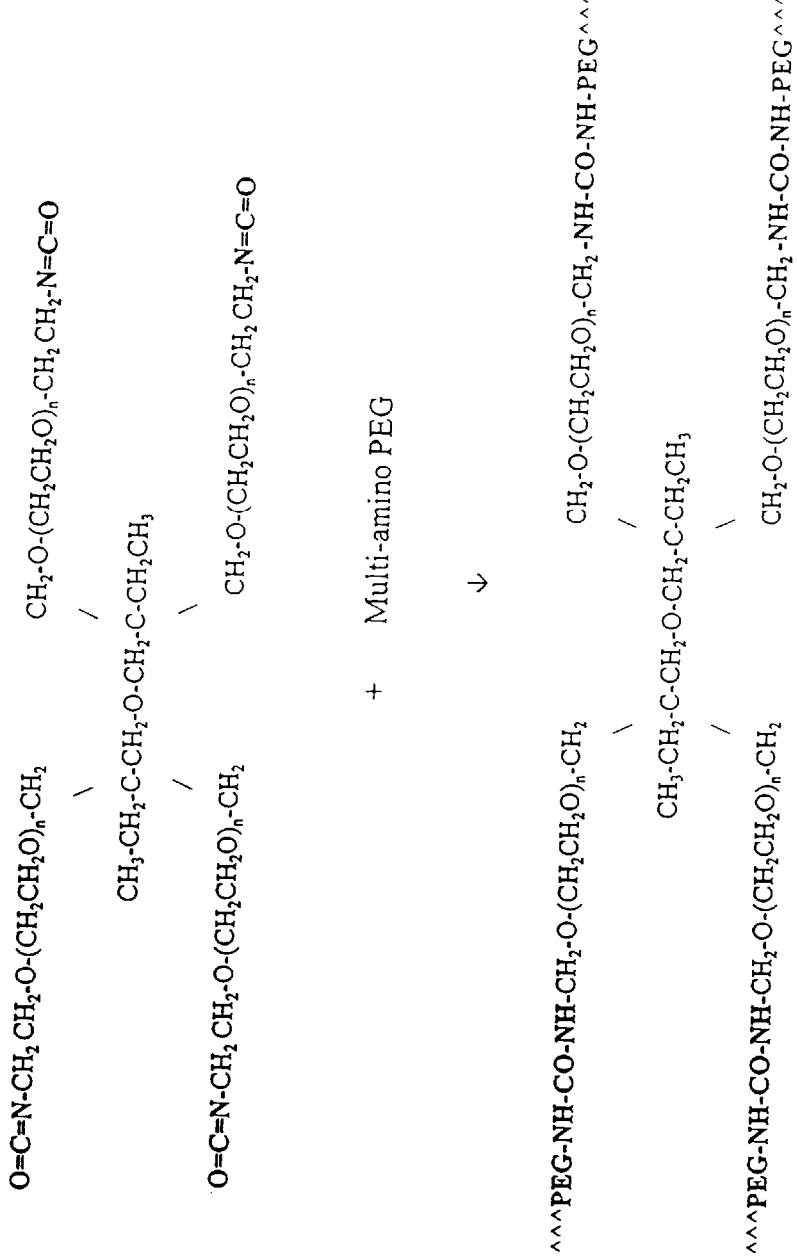

Another activated derivative of polyethylene glycol is functionally activated PEG-isocyanate (I-PEG), which is shown in FIG. 12, along with the conjugate formed by reacting such with multi-amino PEG.

Figure 13:
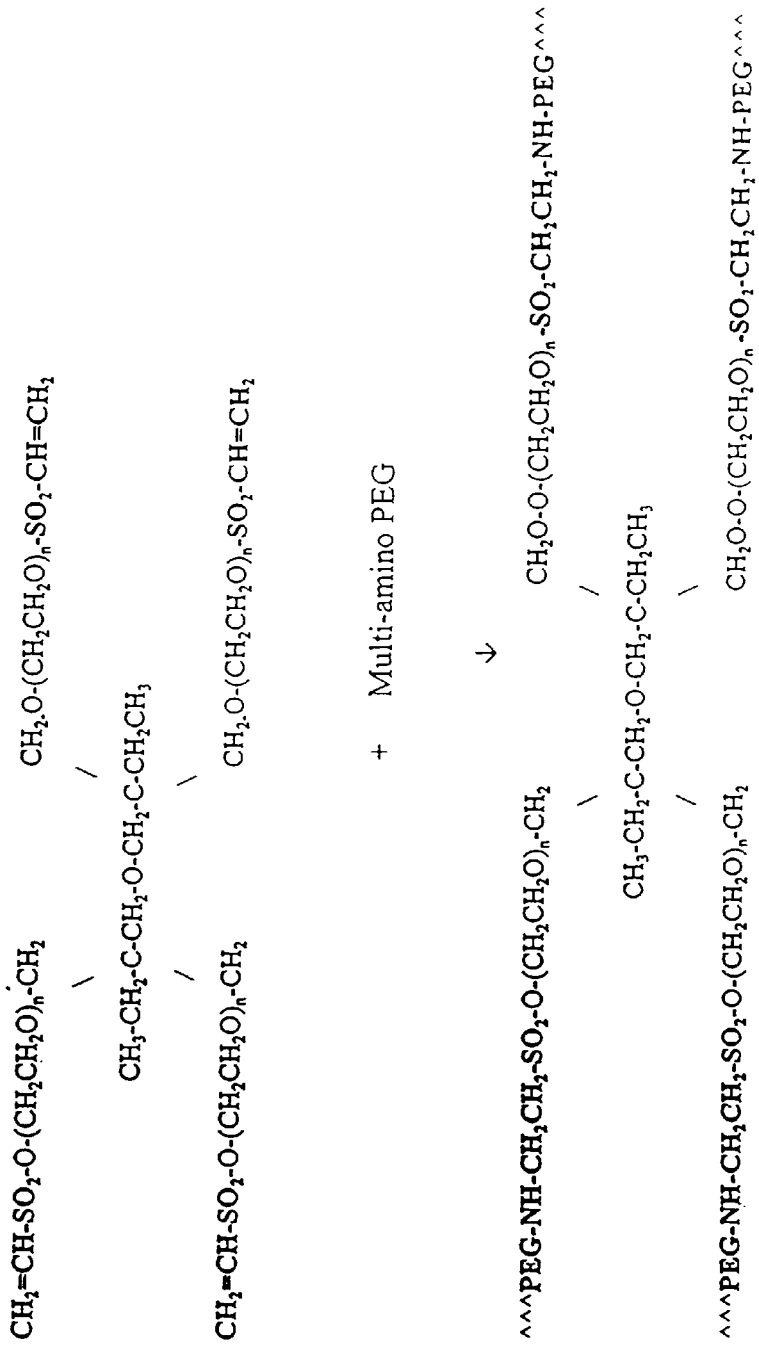
Figure 14:
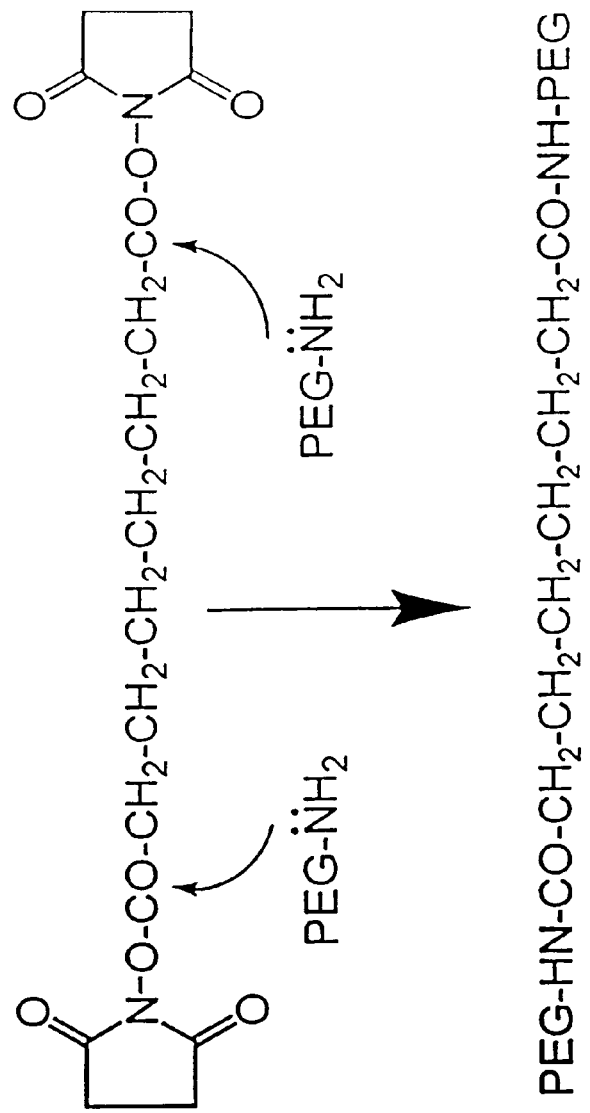
FIGS. 14 to 18 show the formation of various crosslinked synthetic polymer compositions from hydrophobic polymers.
Figure 15:
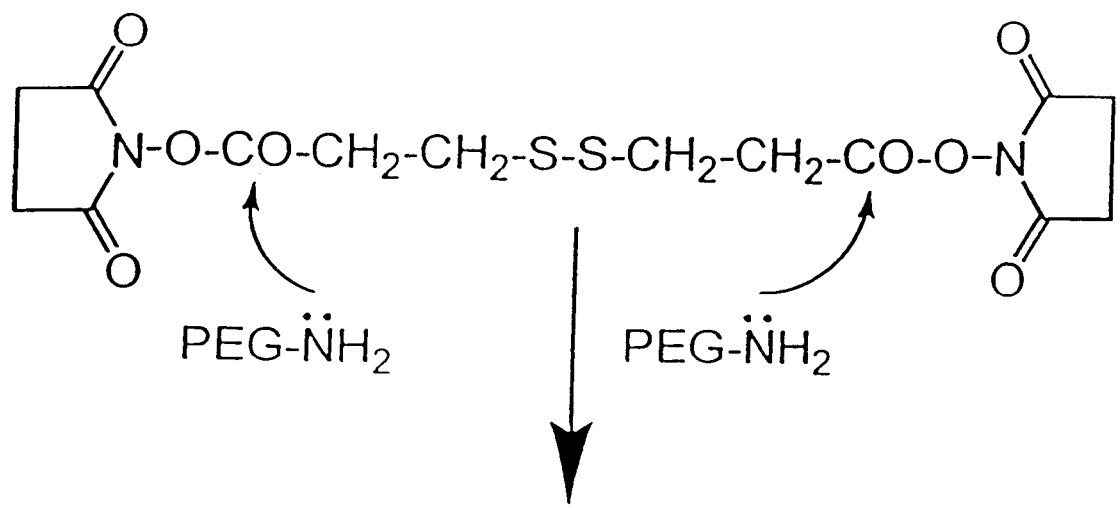
Figure 16:
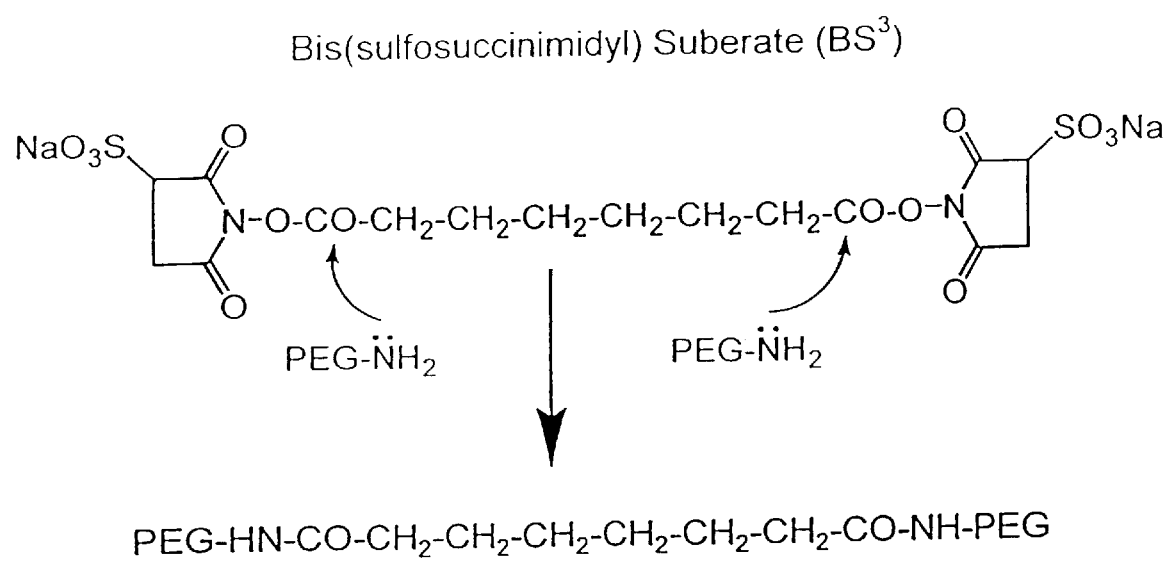
Figure 17:
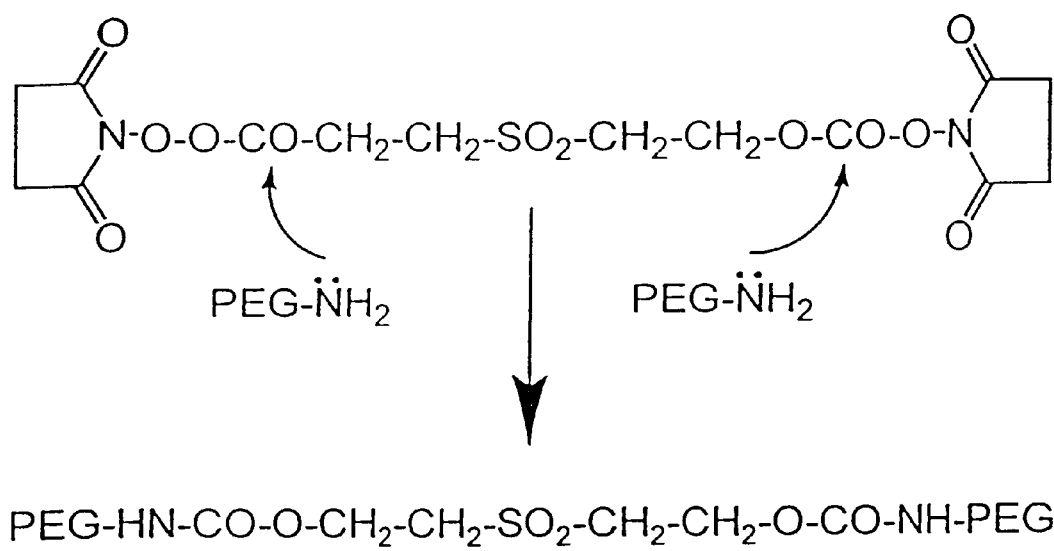
Figure 18:
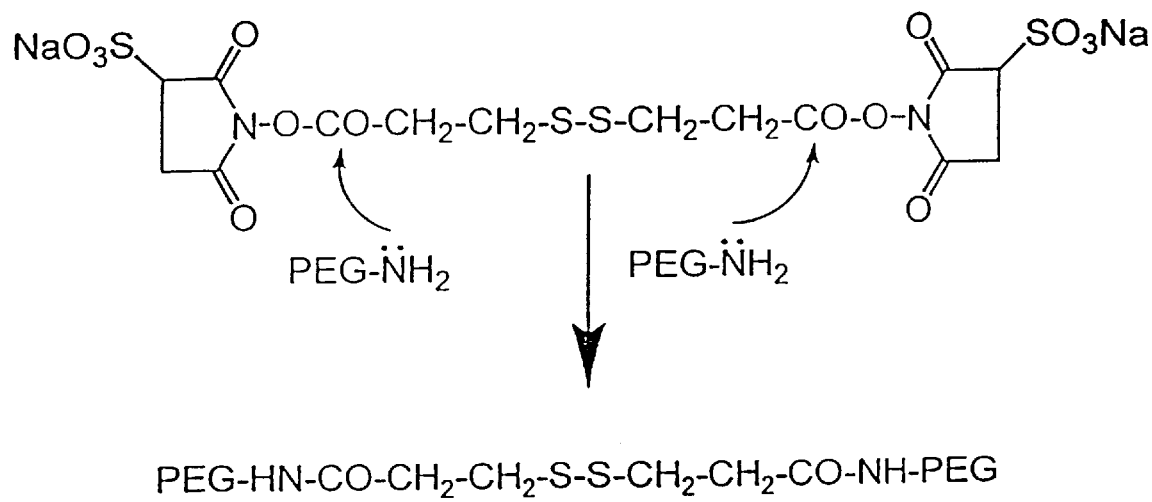

Another activated derivative of polyethylene glycol is functionally activated PEG-vinylsulfone (V-PEG), which is shown in FIG. 13, below, along with the conjugate formed by reacting such with multi-amino PEG.

Preferred multifunctionally activated polyethylene glycols for use in the compositions of the present invention are polyethylene glycols containing succinimidyl groups, such as SG-PEG and SE-PEG (shown in FIGS. 4–7), preferably in trifunctionally or tetrafunctionally activated form.

Many of the activated forms of polyethylene glycol described above are now available commercially from Shearwater Polymers, Huntsville, Ala., and Union Carbide, South Charleston, W. Va.

Hydrophobic Polymers

Hydrophobic polymers can also be used to prepare the compositions of the present invention. Hydrophobic polymers for use in the present invention preferably contain, or can be derivatized to contain two or more electrophilic groups, such as succinimidyl groups, most preferably, two, three, or four electrophilic groups. As used herein, the term "hydrophobic polymer" refers to polymers which contain a relatively small proportion of oxygen or nitrogen atoms.

Hydrophobic polymers which already contain two or more succinimidyl groups include, without limitation, disuccinimidyl suberate (DSS), bis(sulfosuccinimidyl) suberate ($BS^3$), dithiobis(succinimidylpropionate) (DSP), bis(2-succinimidooxycarbonyloxy) ethyl sulfone (BSOCOES), and 3,3'-dithiobis(sulfosuccinimidylpropionate (DTSPP), and their analogs and derivatives. The above-referenced polymers are commercially available from Pierce (Rockford, Ill.), under catalog Nos. 21555, 21579, 22585, 21554, and 21577, respectively. Structural formulas for the above-referenced polymers, as well as generalized reaction products obtained by reacting each of these polymers with amino PEG, are shown below in FIGS. 14–18, respectively.

Preferred hydrophobic polymers for use in the invention generally have a carbon chain that is no longer than about 14 carbons. Polymers having carbon chains substantially longer than 14 carbons generally have very-poor solubility in aqueous solutions and, as such, have very long reaction times when mixed with aqueous solutions of synthetic polymers containing multiple nucleophilic groups.

Derivatization of Polymers to Contain Functional Groups

Certain polymers, such as polyacids, can be derivatized to contain two or more functional groups, such as succinimidyl groups. Polyacids for use in the present invention include, without limitation, trimethylolpropane-based tricarboxylic acid, di(trimethylol propane)-based tetracarboxylic acid, heptanedioic acid, octanedioic acid (suberic acid), and hexadecanedioic acid (thapsic acid). Many of these polyacids are commercially available from DuPont Chemical Company.

According to a general method, polyacids can be chemically derivatized to contain two or more succinimidyl groups by reaction with an appropriate molar amount of N-hydroxysuccinimide (NHS) in the presence of N,N'-dicyclohexylcarbodiimide (DCC).

Polyalcohols such as trimethylolpropane and di(trimethylol propane) can be converted to carboxylic acid form using various methods, then further derivatized by reaction with NHS in the presence of DCC to produce trifunctionally and tetrafunctionally activated polymers, respectively, as described in commonly owned, copending U.S. application Ser. No. 08/403,358. Polyacids such as heptanedioic acid (HOOC—$(CH_2)_5$—COOH), octanedioic acid (HOOC—$(CH_2)_6$—COOH), and hexadecanedioic acid (HOOC—$(CH_2)_{14}$—COOH) are derivatized by the addition of succinimidyl groups to produce difunctionally activated polymers.

Polyamines such as ethylenediamine ($H_2N$—$CH_2CH_2$—$NH_2$), tetramethylenediamine ($H_2N$—$(CH_2)_4$—$NH_2$), pentamethylenediamine (cadaverine) ($H_2N$—$(CH_2)_5$—$NH_2$), hexamethylenediamine ($H_2N$—$(CH_2)_6$—$NH_2$), bis(2-hydroxyethyl)amine (HN—$(CH_2CH_2OH)_2$), bis(2 aminoethyl)amine (HN—$(CH_2CH_2NH_2)_2$), and tris(2-aminoethyl)amine (N—$(CH_2CH_2NH_2)_3$) can be chemically derivatized to polyacids, which can then be derivatized to contain two or more succinimidyl groups by reacting with the appropriate molar amounts of N-hydroxysuccinimide in the presence of DCC, as described in U.S. application Ser. No. 08/403,358. Many of these polyamines are commercially available from DuPont Chemical Company.

Preparation of Crosslinked Polymer Compositions

In a general method for preparing the crosslinked polymer compositions of the invention, a first synthetic polymer containing multiple nucleophilic groups is mixed with a second synthetic polymer containing multiple electrophilic groups. Formation of a three-dimensional crosslinked network occurs as a result of the reaction between the nucleophilic groups on the first synthetic polymer and the electrophilic groups on the second synthetic polymer.

Hereinafter, the term "first synthetic polymer" will be used to refer to a synthetic polymer containing two or more nucleophilic groups, and the term "second synthetic polymer" will be used to refer to a synthetic polymer containing two or more electrophilic groups. The concentrations of the first synthetic polymer and the second synthetic polymer used to prepare the compositions of the present invention will vary depending upon a number of factors, including the types and molecular weights of the particular synthetic polymers used and the desired end use application.

In general, we have found that when using multi-amino PEG as the first synthetic polymer, it is preferably used at a concentration in the range of about 0.5 to about 20 percent by weight of the final composition, while the second synthetic polymer is used at a concentration in the range of about 0.5 to about 20 percent by weight of the final composition. For example, a final composition having a total weight of 1 gram (1000 milligrams) would contain between about 5 to about 200 milligrams of multi-amino PEG, and between about 5 to about 200 milligrams of the second synthetic polymer.

Use of higher concentrations of both first and second synthetic polymers will result in the formation of a more tightly crosslinked network, producing a stiffer, more robust gel. As such, compositions intended for use in tissue augmentation will generally employ concentrations of first and second synthetic polymer that fall toward the higher end of the preferred concentration range. Compositions intended for use as bioadhesives or in adhesion prevention do not need to be as firm and may therefore contain lower polymer concentrations.

Because polymers containing multiple electrophilic groups will also react with water, the second synthetic polymer is generally stored and used in sterile, dry form to prevent the loss of crosslinking ability due to hydrolysis which typically occurs upon exposure of such electrophilic groups to aqueous media. Processes for preparing synthetic hydrophilic polymers containing multiple electrophylic groups in sterile, dry form are set forth in commonly assigned, copending U.S. application Ser. No. 08/497,573, filed Jun. 30, 1995. For example, the dry synthetic polymer may be compression molded into a thin sheet or membrane, which can then be sterilized using gamma or, preferably, e-beam irradiation. The resulting dry membrane or sheet can be cut to the desired size or chopped into smaller size particulates.

Polymers containing multiple nucleophilic groups are generally not water-reactive and can therefore be stored in aqueous solution.

The crosslinked polymer compositions can also be prepared to contain various imaging agents such as iodine or barium sulfate, or fluorine, in order to aid visualization of the compositions after administration via X-ray, or $^{19}$F-MRI, respectively.

Incorporation of Other Components into the Crosslinked Synthetic Polymer

Naturally occurring proteins, such as collagen, and derivatives of various naturally occurring polysaccharides, such as glycosaminoglycans, can additionally be incorporated into the compositions of the invention. When these other components also contain functional groups which will react with the functional groups on the synthetic polymers, their presence during mixing and/or crosslinking of the first and second synthetic polymer will result in formation of a crosslinked synthetic polymer-naturally occurring polymer matrix. In particular, when the naturally occurring polymer (protein or polysaccharide) also contains nucleophilic groups such as primary amino groups, the electrophilic groups on the second synthetic polymer will react with the primary amino groups on these components, as well as the nucleophilic groups on the first synthetic polymer, to cause these other components to become part of the polymer matrix.

In general, glycosaminoglycans must be chemically derivatized by deacetylation, desulfation, or both in order to contain primary amino groups available for reaction with electrophilic groups on synthetic polymer molecules. Glycosaminoglycans that can be derivatized according to either or both of the aforementioned methods include the following: hyaluronic acid, chondroitin sulfate A, chondroitin sulfate B (dermatan sulfate), chondroitin sulfate C, chitin (can be derivatized to chitosan), keratan sulfate, keratosulfate, and heparin. Derivatization of glycosaminoglycans by deacetylation and/or desulfation and covalent binding of the resulting glycosaminoglycan derivatives with synthetic hydrophilic polymers is described in further detail in commonly assigned, allowed U.S. patent application Ser. No. 08/146,843, filed Nov. 3, 1993.

Similarly, electrophilic groups on the second synthetic polymer will react with primary amino groups on lysine residues or thiol groups on cysteine residues of certain naturally occurring proteins. Lysine-rich proteins such as collagen and its derivatives are especially reactive with electrophilic groups on synthetic polymers. As used herein, the term "collagen" is intended to encompass collagen of any type, from any source, including, but not limited to, collagen extracted from tissue or produced recombinantly, collagen analogues, collagen derivatives, modified collagens, and denatured collagens such as gelatin. Covalent binding of collagen to synthetic hydrophilic polymers is described in detail in commonly assigned U.S. Pat. No. 5,162,430, issued Nov. 10, 1992, to Rhee et al.

In general, collagen from any source may be used in the compositions of the invention; for example, collagen may be extracted and purified from human or other mammalian source, such as bovine or porcine corium and human placenta, or may be recombinantly or otherwise produced. The preparation of purified, substantially non-antigenic collagen in solution from bovine skin is well known in the art. Commonly owned, U.S. Pat. No. 5,428,022, issued Jun. 27, 1995, to Palefsky et al., discloses methods of extracting and purifying collagen from the human placenta. Commonly owned, copending U.S. application Ser. No. 08/183,648, filed Jan. 18, 1994, discloses methods of producing recombinant human collagen in the milk of transgenic animals, including transgenic cows. The term "collagen" or "collagen material" as used herein refers to all forms of collagen, including those which have been processed or otherwise modified.

Collagen of any type, including, but not limited to, types I, II, III, IV, or any combination thereof, may be used in the compositions of the invention, although type I is generally preferred. Either atelopeptide or telopeptide-containing collagen may be used; however, when collagen from a xenogeneic source, such as bovine collagen, is used, atelopeptide collagen is generally preferred, because of its reduced immunogenicity compared to telopeptide-containing collagen.

Collagen that has not been previously crosslinked by methods such as heat, irradiation, or chemical crosslinking agents is preferred for use in the compositions of the invention, although previously crosslinked collagen may be used. Non-crosslinked atelopeptide fibrillar collagen is commercially available from Collagen Corporation (Palo Alto, Calif.) at collagen concentrations of 35 mg/ml and 65 mg/ml under the trademarks Zyderm® I Collagen and Zyderm II Collagen, respectively. Glutaraldehyde crosslinked atelopeptide fibrillar collagen is commercially available from Collagen Corporation at a collagen concentration of 35 mg/ml under-the trademark Zyplast® Collagen.

Collagens for use in the present invention are generally in aqueous suspension at a concentration between about 20 mg/ml to about 120 mg/ml; preferably, between about 30 mg/ml to about 90 mg/ml.

Although intact collagen is preferred, denatured collagen, commonly known as gelatin, can also be used in the compositions of the invention. Gelatin may have the added benefit of being degradable faster than collagen.

Because of its tacky consistency, nonfibrillar collagen is generally preferred for use in compositions of the invention that are intended for use as bioadhesives. The term "nonfibrillar collagen" refers to any modified or unmodified collagen material that is in substantially nonfibrillar form at pH 7, as indicated by optical clarity of an aqueous suspension of the collagen.

Collagen that is already in nonfibrillar form may be used in the compositions of the invention. As used herein, the term "nonfibrillar collagen" is intended to encompass collagen types that are nonfibrillar in native form, as well as collagens that have been chemically modified such that they are in nonfibrillar form at or around neutral pH. Collagen types that are nonfibrillar (or microfibrillar) in native form include types IV, VI, and VII.

Chemically modified collagens that are in nonfibrillar form at neutral pH include succinylated collagen and methylated collagen, both of which can be prepared according to the methods described in U.S. Pat. No. 4,164,559, issued Aug. 14, 1979, to Miyata et al., which is hereby incorporated by reference in its entirety. Due to its inherent tackiness, methylated collagen is particularly preferred for use in bioadhesive compositions, as disclosed in commonly owned, U.S. application Ser. No. 08/476,825.

Collagens for use in the crosslinked polymer compositions of the present invention may start out in fibrillar form, then be rendered nonfibrillar by the addition of one or more fiber disassembly agent. The fiber disassembly agent must be present in an amount sufficient to render the collagen substantially nonfibrillar at pH 7, as described above. Fiber disassembly agents for use in the present invention include, without limitation, various biocompatible alcohols, amino acids, inorganic salts, and carbohydrates, with biocompatible alcohols being particularly preferred. Preferred biocompatible alcohols include glycerol and propylene glycol. Non-biocompatible alcohols, such as ethanol, methanol, and isopropanol, are not preferred for use in the present invention, due to their potentially deleterious effects on the body of the patient receiving them. Preferred amino acids include arginine. Preferred inorganic salts include sodium chloride and potassium chloride. Although carbohydrates, such as various sugars including sucrose, may be used in the practice of the present invention, they are not as preferred as other types of fiber disassembly agents because they can have cytotoxic effects in vivo.

Because it is opaque and less tacky than nonfibillar collagen, fibrillar collagen is less preferred for use in bioadhesive compositions. However, as disclosed in commonly owned, U.S. application Ser. No. 08/476,825, fibrillar collagen, or mixtures of nonfibrillar and fibrillar collagen, may be preferred for use in adhesive compositions intended for long-term persistence in vivo, if optical clarity is not a requirement.

For compositions intended for use in tissue augmentation, fibrillar collagen is preferred because it tends to form stronger crosslinked gels having greater long-term persistency in vivo than those prepared using nonfibrillar collagen.

In general, the collagen is added to the first synthetic polymer, then the collagen and first synthetic polymer are mixed thoroughly to achieve a homogeneous composition. The second synthetic polymer is then added and mixed into the collagen/first synthetic polymer mixture, where it will covalently bind to primary amino groups or thiol groups on the first synthetic polymer and primary amino groups on the collagen, resulting in the formation of a homogeneous crosslinked network. Various deacetylated and/or desulfated glycosaminoglycan derivatives can be incorporated into the composition in a similar manner as that described above for collagen.

For use in tissue adhesion as discussed below, it may also be desirable to incorporate proteins such as albumin, fibrin or fibrinogen into the crosslinked polymer composition to promote cellular adhesion.

In addition, the introduction of hydrocolloids such as carboxymethylcellulose may promote tissue adhesion and/or swellability.

Administration of the Crosslinked Synthetic Polymer Compositions

The compositions of the present invention may be administered before, during or after crosslinking of the first and second synthetic polymer. Certain uses, which are discussed in greater detail below, such as tissue augmentation, may require the compositions to be crosslinked before administration, whereas other applications, such as tissue adhesion, require the compositions to be administered before crosslinking has reached "equilibrium." The point at which crosslinking has reached equilibrium is defined herein as the point at which the composition no longer feels tacky or sticky to the touch.

In order to administer the composition prior to crosslinking, the first synthetic polymer and second synthetic polymer may be contained within separate barrels of a dual-compartment syringe. In this case, the two synthetic polymers do not actually mix until the point at which the two polymers are extruded from the tip of the syringe needle into the patient's tissue. This allows the vast majority of the crosslinking reaction to occur in situ, avoiding the problem of needle blockage which commonly occurs if the two synthetic polymers are mixed too early and crosslinking between the two components is already too advanced prior to delivery from the syringe needle. The use of a dual-compartment syringe, as described above, allows for the use of smaller diameter needles, which is advantageous when performing soft tissue augmentation in delicate facial tissue, such as that surrounding the eyes.

Alternatively, the first synthetic polymer and second synthetic polymer may be mixed according to the methods described above prior to delivery to the tissue site, then injected to the desired tissue site immediately (preferably, within about 60 seconds) following mixing.

In another embodiment of the invention, the first synthetic polymer and second synthetic polymer are mixed, then extruded and allowed to crosslink into a sheet or other solid form. The crosslinked solid is then dehydrated to remove substantially all unbound water. The resulting dried solid may be ground or comminuted into particulates, then suspended in a nonaqueous fluid carrier, including, without limitation, hyaluronic acid, dextran sulfate, dextran, succinylated noncrosslinked collagen, methylated noncrosslinked collagen, glycogen, glycerol, dextrose, maltose, triglycerides of fatty acids (such as corn oil, soybean oil, and sesame oil), and egg yolk phospholipid. The suspension of particulates can be injected through a small-gauge needle to a tissue site. Once inside the tissue, the crosslinked polymer particulates will rehydrate and swell in size at least five-fold.

Use of Crosslinked Synthetic Polymers to Deliver Charged Compounds

By varying the relative molar amounts of the first synthetic polymer and the second synthetic polymer, it is possible to alter the net charge of the resulting crosslinked polymer composition, in order to prepare a matrix for the delivery of a charged compound (such as a protein or drug). As such, the delivery of charged proteins or drugs, which would normally diffuse rapidly out of a neutral carrier matrix, can be controlled.

For example, if a molar excess of a first synthetic polymer containing multiple nucleophilic groups is used, the resulting matrix has a net positive charge and can be used to ionically bind and deliver negatively charged compounds. Examples of negatively charged compounds that can be delivered from these matrices include various drugs, cells, proteins, and polysaccharides. Negatively charged collagens, such as succinylated collagen, and glycosaminoglycan derivatives, such as sodium hyaluronate, keratan sulfate, keratosulfate, sodium chondroitin sulfate A, sodium dermatan sulfate B, sodium chondroitin sulfate C, heparin, esterified chondroitin sulfate C, and esterified heparin, can be effectively incorporated into the crosslinked polymer matrix as described above.

If a molar excess of a second synthetic polymer containing multiple electrophilic groups is used, the resulting matrix has a net negative charge and can be used to ionically bind and deliver positively charged compounds. Examples of positively charged compounds that can be delivered from these matrices include various drugs, cells, proteins, and polysaccharides. Positively charged collagens, such as methylated collagen, and glycosaminoglycan derivatives, such as esterified deacetylated hyaluronic acid, esterified deacetylated desulfated chondroitin sulfate A, esterified deacetylated desulfated chondroitin sulfate C, deacetylated desulfated keratan sulfate, deacetylated desulfated keratosulfate, esterified desulfated heparin, and chitosan, can be effectively incorporated into the crosslinked polymer matrix as described above.

Use of Crosslinked Synthetic Polymers to Deliver Biologically Active Agents

The crosslinked polymer compositions of the present invention may also be used for localized delivery of various drugs and other biologically active agents. Biologically active agents such as growth factors may be delivered from the composition to a local tissue site in order to facilitate tissue healing and regeneration.

The term "biologically active agent" or "active agent" as used herein refers to organic molecules which exert biological effects in vivo. Examples of active agents include, without limitation, enzymes, receptor antagonists or agonists, hormones, growth factors, autogenous bone marrow, antibiotics, antimicrobial agents and antibodies. The term "active agent" is also intended to encompass various cell types and genes which can be incorporated into the compositions of the invention. The term "active agent" is also intended to encompass combinations or mixtures of two or more active agents, as defined above.

Preferred active agents for use in the compositions of the present invention include growth factors, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are particularly preferred. Members of the TGF supergene family include the beta transforming growth factors (for example, TGF-$\beta$1, TGF-$\beta$2, TGF-$\beta$3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); inhibins (for example, Inhibin A, Inhibin B); growth differentiating factors (for example, GDF-1); and Activins (for example, Activin A, Activin B, Activin AB).

Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Biologically active agents may be incorporated into the crosslinked synthetic polymer composition by admixture. Alternatively, the agents may be incorporated into the crosslinked polymer matrix, as described above, by binding these agents with the functional groups on the synthetic polymers. Processes for covalently binding biologically active agents such as growth factors using functionally activated polyethylene glycols are described in commonly assigned U.S. Pat. No. 5,162,430, issued Nov. 10, 1992, to Rhee et al. Such compositions preferably include linkages that can be easily biodegraded, for example as a result of enzymatic degradation, resulting in the release of the active agent into the target tissue, where it will exert its desired therapeutic effect.

A simple method for incorporating biologically active agents containing nucleophilic groups into the crosslinked polymer composition involves mixing the active agent with the first synthetic polymer (or first synthetic polymer/collagen mixture) prior to adding the second synthetic polymer. This procedure will result in covalent binding of the active agent to the crosslinked polymer composition, producing a highly effective sustained release composition.

The type and amount of active agent used will depend, among other factors, on the particular site and condition to be treated and the biological activity and pharmacokinetics of the active agent selected.

Use of Crosslinked Synthetic Polymers to Deliver Cells or Genes

The crosslinked polymer compositions of the present invention can also be used to deliver various types of living cells or genes to a desired site of administration in order to form new tissue. The term "genes" as used herein is intended to encompass genetic material from natural sources, synthetic nucleic acids, DNA, antisense-DNA and RNA.

When used to deliver cells, for example, mesenchymal stem cells can be delivered to produce cells of the same type as the tissue into which they are delivered. Mesenchymal stem cells are not differentiated and therefore can differentiate to form various types of new cells due to the presence of an active agent or the effects (chemical, physical, etc.) of the local tissue environment. Examples of mesenchymal stem cells include osteoblasts, chondrocytes, and fibroblasts. Osteoblasts can be delivered to the site of a bone defect to produce new bone; chondrocytes can be delivered to the site of a cartilage defect to produce new cartilage; fibroblasts can be delivered to produce collagen wherever new connective tissue is needed; neurectodermal cells can be delivered to form new nerve tissue; epithelial cells can be delivered to form new epithelial tissues, such as liver, pancreas, etc.

The cells or genes may be either allogeneic or xenogeneic in origin. For example, the compositions can be used to deliver cells or genesfrom other species which have been genetically modified. Because the compositions of the invention are not easily degraded in vivo, cells and genes entrapped within the crosslinked polymer compositions will be isolated from the patient's own cells and, as such, will not provoke an immune response in the patient. In order to entrap the cells or genes within a crosslinked polymer matrix, the first polymer and the cells or genes may be pre-mixed, then the second polymer is mixed into the first polymer/cell or gene mixture to form a crosslinked matrix, thereby entrapping the cells or genes within the matrix.

As discussed above for biologically active agents, when used to deliver cells or genes, the synthetic polymers preferably also contain biodegradable groups to aid in controlled release of the cells or genes at the intended site of delivery.

Use of the Crosslinked Synthetic Polymers as Bioadhesives

We have found that the preferred compositions of the invention tend to have unusually high tackiness, making them particularly suitable for use as bioadhesives, for example, for use in surgery. As used herein, the terms "bioadhesive", "biological adhesive", and "surgical adhesive" are used interchangeably to refer to biocompatible compositions capable of effecting temporary or permanent attachment between the surfaces of two native tissues, or between a native tissue surface and a non-native tissue surface or a surface of a synthetic implant.

In a general method for effecting the attachment of a first surface to a second surface, the first synthetic polymer and the second synthetic polymer are applied to a first surface, then the first surface is contacted with a second surface to effect adhesion between the first surface and the second surface. Preferably, the first synthetic polymer and second synthetic polymer are first mixed to initiate crosslinking, then delivered to a first surface before substantial crosslinking has occurred between the nucleophilic groups on the first synthetic polymer and the electrophilic groups on the second synthetic polymer. The first surface is then contacted with the second surface, preferably immediately, to effect adhesion between the two surfaces. At least one of the first and second surfaces is preferably a native tissue surface.

For example, the first synthetic polymer and second synthetic polymer are generally provided in separate syringes, the contents of which are then mixed together using syringe-to-syringe mixing techniques just prior to delivery to a first surface. The first synthetic polymer and second synthetic polymer are preferably mixed for a minimum of 20 (preferably, 20 to 100; more preferably, 30 to 60) passes to ensure adequate mixing. As crosslinking between the corresponding reactive groups on the two synthetic polymers is generally initiated during the mixing process, it is important to deliver the reaction mixture to the first surface as soon as possible after mixing.

The reaction mixture can be extruded onto the first surface from the opening of a syringe or other appropriate extrusion device. Following application, the extruded reaction mixture can be spread over the first surface using a spatula, if necessary. Alternatively, the first synthetic polymer and the second synthetic polymer can be mixed together in an appropriate mixing dish or vessel, then applied to the first surface using a spatula In another method for preparing the reaction mixture, the first synthetic polymer and second synthetic polymer are contained in separate chambers of a spray can or bottle with a nozzle, or other appropriate spraying device. In this scenario, the first and second polymers do not actually mix until they are expelled together from the nozzle of the spraying device. Following application of the reaction mixture to a surface containing collagen, the first surface is contacted with a second surface. If the two surfaces are contacted before substantial crosslinking has occurred between the synthetic polymer and the crosslinking agent, the reactive groups on the crosslinking agent will also covalently bond with primary amino groups on lysine residues of collagen molecules present on either or both of the surfaces, providing improved adhesion.

The two surfaces may be held together manually, or using other appropriate means, while the crosslinking reaction is proceeding to completion. Crosslinking is typically complete within 5 to 60 minutes after mixing of the first and second synthetic polymers. However, the time required for complete crosslinking to occur is dependent on a number of factors, including the types and molecular weights of the two synthetic polymers and, most particularly, the concentrations of the two synthetic polymers (i.e., higher concentrations result in faster crosslinking times).

At least one of the first and second surfaces is preferably a native tissue surface. As used herein, the term "native tissue" refers to biological tissues that are native to the body of the specific patient being treated. As used herein, the term "native tissue" is intended to include biological tissues that have been elevated or removed from one part of the body of a patient for implantation to another part of the body of the same patient (such as bone autografts, skin flap autografts, etc.). For example, the compositions of the invention can be used to adhere a piece of skin from one part of a patient's body to another part of the body, as in the case of a burn victim.

The other surface may be a native tissue surface, a non-native tissue surface, or a surface of a synthetic implant. As used herein, the term "non-native tissue" refers to biological tissues that have been removed from the body of a donor patient (who may be of the same species or of a different species than the recipient patient) for implantation into the body of a recipient patient (e.g., tissue and organ transplants). For example, the crosslinked polymer compositions of the present invention can be used to adhere a donor cornea to the eye of a recipient patient.

As used herein, the term "synthetic implant" refers to any biocompatible material intended for implantation into the body of a patient not encompassed by the above definitions for native tissue and non-native tissue. Synthetic implants include, for example, artificial blood vessels, heart valves, artificial organs, bone prostheses, implantable lenticules, vascular grafts, stents, and stent/graft combinations, etc.

Use of Crosslinked Synthetic Polymers in Ophthalmic Applications

Because of their optical clarity, the crosslinked polymer compositions of the invention which do not contain collagen are particularly well suited for use in ophthalmic applications. For example, a synthetic lenticule for correction of vision can be attached to the Bowman's layer of the cornea of a patient's eye using the methods of the present invention. As disclosed in commonly assigned, allowed U.S. application Ser. No. 08/147,227, filed Nov. 3,1993, by Rhee et al., a chemically modified collagen (such as succinylated or methylated collagen) which is in substantially nonfibrillar form at pH 7 can be crosslinked using a synthetic hydrophilic polymer, then molded into a desired lenticular shape and allowed to complete crosslinking. The resulting crosslinked collagen lenticule can then be attached to the Bowman's layer of a de-epithelialized cornea of a patient's eye using the methods of the present invention. By applying the reaction mixture comprising the first and second synthetic polymers to the anterior surface of the cornea, then contacting the anterior surface of the cornea with the posterior surface of the lenticule before substantial crosslinking has occurred, electrophilic groups on the second synthetic polymer will also covalently bind with collagen molecules in both the corneal tissue and the lenticule to firmly anchor the lenticule in place. (Alternatively, the reaction mixture can be applied first to the posterior surface of the lenticule, which is then contacted with the anterior surface of the cornea.)

The compositions of the present invention are also suitable for use in vitreous replacement.

Use of Crosslinked Synthetic Polymer Compositions in Tissue Augmentation

The crosslinked polymer compositions of the invention can also be used for augmentation of soft or hard tissue within the body of a mammalian subject.

As such, they may be better than currently marketed collagen-based materials product for soft tissue augmentation, because they are less immunogenic and more persistent. Examples of soft tissue augmentation applications include sphincter (e.g., urinary, anal, esophageal) sphincter augmentation and the treatment of rhytids and scars. Examples of hard tissue augmentation applications include the repair and/or replacement of bone and/or cartilaginous tissue.

The compositions of the invention are particularly suited for use as a replacement material for synovial fluid in osteoarthritic joints, where the crosslinked polymer compositions serve to reduce joint pain and improve joint function by restoring a soft hydrogel network in the joint. The crosslinked polymer compositions can also be used as a replacement material for the nucleus pulposus of a damaged intervertebral disk. As such, the nucleus pulposus of the damaged disk is first removed, then the crosslinked polymer composition is injected or otherwise introduced into the center of the disk. The composition may either be crosslinked prior to introduction into the disk, or allowed to crosslink in situ.

In a general method for effecting augmentation of tissue within the body of a mammalian subject, the first and second synthetic polymers are injected simultaneously to a tissue site in need of augmentation through a small-gauge (e.g., 25–32 gauge) needle. Once inside the patient's body, the nucleophilic groups on the first synthetic polymer and the electrophilic groups on the second synthetic polymer will react with each other to form a crosslinked polymer network in situ. Electrophilic groups on the second synthetic polymer may also react with primary amino groups on lysine residues of collagen molecules within the patient's own tissue, providing for "biological anchoring" of the compositions with the host tissue.

Use of the Crosslinked Synthetic Polymer Compositions to Prevent Adhesions

Another use of the crosslinked polymer compositions of the invention is to coat tissues in order to prevent the formation of adhesions following surgery or injury to internal tissues or organs. In a general method for coating tissues to prevent the formation of adhesions following surgery, the first and second synthetic polymers are mixed, then a thin layer of the reaction mixture is applied to the tissues comprising, surrounding, and/or adjacent to the surgical site before substantial crosslinking has occurred between the nucleophilic groups on the first synthetic polymer and the electrophilic groups on the second synthetic polymer. Application of the reaction mixture to the tissue site may be by extrusion, brushing, spraying (as described above), or by any other convenient means.

Following application of the reaction mixture to the surgical site, crosslinking is allowed to continue in situ prior to closure of the surgical incision. Once crosslinking has reached equilibrium, tissues which are brought into contact with the coated tissues will not stick to the coated tissues. At this point in time, the surgical site can be closed using conventional means (sutures, etc.).

In general, compositions that achieve complete crosslinking within a relatively short period of time (i.e., 5–15 minutes following mixture of the first synthetic polymer and the second synthetic polymer) are preferred for use in the prevention of surgical adhesions, so that the surgical site may be closed relatively soon after completion of the surgical procedure.

Use of the Crosslinked Synthetic Polymers to Coat Implants

Another use of the crosslinked polymer compositions of the invention is as a coating material for synthetic implants. In a general method for coating a surface of a synthetic implant, the first and second synthetic polymers are mixed, then a thin layer of the reaction mixture is applied to a surface of the implant before substantial crosslinking has occurred between the nucleophilic groups on the first synthetic polymer and the electrophilic groups on the second synthetic polymer. In order to minimize cellular and fibrous reaction to the coated implant, the reaction mixture is preferably prepared to have a net neutral charge. Application of the reaction mixture to the implant surface may be by extrusion, brushing, spraying (as described above), or by any other convenient means. Following application of the reaction mixture to the implant surface, crosslinking is allowed to continue until complete crosslinking has been achieved.

Although this method can be used to coat the surface of any type of synthetic implant, it is particularly useful for implants where reduced thrombogenicity is an important consideration, such as artificial blood vessels and heart valves, vascular grafts, vascular stents, and stent/graft combinations. The method may also be used to coat implantable surgical membranes (e.g., monofilament polypropylene) or meshes (e.g., for use in hernia repair). Breast implants may also be coated using the above method in order to minimize capsular contracture.

The compositions of the present invention may also be used to coat lenticules, which are made from either naturally occurring or synthetic polymers.

Use of the Crosslinked Synthetic Polymers to Treat Aneurism

The crosslinked polymer compositions of the invention can be extruded or molded in the shape of a string or coil, then dehydrated. The resulting dehydrated string or coil can be delivered via catheter to the site of a vascular malformation, such as an aneurysm, for the purpose of vascular occlusion and, ultimately, repair of the malformation. The dehydrated string or coil can be delivered in a compact size and will rehydrate inside the blood vessel, swelling several times in size compared to its dehydrated state, while maintaining its original shape.

Other Uses for the Crosslinked Synthetic Polymers

As discussed in commonly assigned, copending application Ser. No. 08/574,050, filed Dec. 18, 1995, which is incorporated herein by reference, the crosslinked polymer compositions of the invention can be used to block or fill various lumens and voids in the body of a mammalian subject. The compositions can also be used as biosealants to seal fissures or crevices within a tissue or structure (such as a vessel), or junctures between adjacent tissues or structures, to prevent leakage of blood or other biological fluids.

The crosslinked polymer compositions can also be used as a large space-filling device for organ displacement in a body cavity during surgical or radiation procedures, for example, to protect the intestines during a planned course of radiation to the pelvis.

The crosslinked polymer compositions of the invention can also be coated onto the interior surface of a physiological lumen, such as a blood vessel or Fallopian tube, thereby serving as a sealant to prevent restenosis of the lumen following medical treatment, such as, for example, balloon catheterization to remove arterial plaque deposits from the interior surface of a blood vessel, or removal of scar tissue or endometrial tissue from the interior of a Fallopian tube. A thin layer of the reaction mixture is preferably applied to the interior surface of the vessel (for example, via catheter) immediately following mixing of the first and second synthetic polymers. Because the compositions of the invention are not readily degradable in vivo, the potential for restenosis due to degradation of the coating is minimized. The use of crosslinked polymer compositions having a net neutral charge further minimizes the potential for restenosis.

EXAMPLES

The following examples are put forth so as to provide those of ordinary skill in the art with a complete disclosure and description of how to make the preferred embodiments of the conjugates, compositions, and devices and are not intended to limit the scope of what the inventors regard as their invention. Efforts have been made to ensure accuracy with respect to numbers used (e.g., amounts, temperature, molecular weight, etc.) but some experimental errors and deviation should be accounted for. Unless indicated otherwise, parts are parts by weight, molecular weight is weight average molecular weight, temperature is in degrees Centigrade, and pressure is at or near atmospheric.

Example 1

Preparation of Crosslinked Multi-amino PEG Compositions 0.15 grams of di-amino PEG (3400 MW, obtained from Shearwater Polymers, Huntsville, Ala.) in 250 ul of water was mixed with 0.1 g of trifunctionally activated SC-PEG (5000 MW, also obtained from Shearwater Polymers) using syringe-to-syringe mixing. The reaction mixture was extruded onto a petri dish and formed a soft gel at room temperature.

0.15gram of di-amino PEG in 250 µl of water was mixed with 0.1 g of tetrafunctionally activated SE-PEG (also from Shearwater Polymers) using syringe-to-syringe mixing. The reaction mixture was extruded onto a petri dish and formed a soft gel at room temperature.

Example 2

Preparation of Crosslinked Multi-amino PEG Compositions

The following stock solutions of various di-amino PEGs were prepared:

Ten (10) grams of Jeffamine ED-2001 (obtained from Texaco Chemical Company, Houston, Tex.) was dissolved in 9 ml of water.

Ten (10) grams of Jeffamine ED4000 (also obtained from Texaco Chemical Company) was dissolved in 9 ml of water.

0.1 grams of di-amino PEG (3400 MW, obtained from Shearwater Polymers, Huntsville, Ala.) was dissolved in 300 µl of water.

Each of the three di-amino PEG solutions prepared above was mixed with aqueous solutions of trifunctionally activated SC-PEG (TSC-PEG, 5000 MW, also obtained from Shearwater Polymers) as set forth in Table 1, below.

TABLE 1

Preparation of Crosslinked Polymer Compositions

| Di-amino PEG | TSC-PEG + Aqueous Solvent |
|---|---|
| 50 ul | 0 mg + 50 µl water |
| 50 ul | 10 mg + 50 µl PBS |
| 50 ul | 10 mg + 100 µl PBS |
| 250 ul | 50 mg + 500 µl PBS |

The solutions of di-amino PEG and TSC-PEG were mixed using syringe-to-syringe mixing. Each of the materials was extruded from the syringe and allowed to set for 1 hour at 37° C. Each of the materials formed a gel. In general, the gels became softer with increasing water content; the gels containing the least amount of aqueous solvent (water or PBS) were firmest.

Example 3

Characterization of Crosslinked Multi-amino PEG Compositions

Fifty (50) milligrams of tetra-amino PEG (10,000 MW, obtained from Shearwater Polymers, Huntsville, Ala.) in 0.5 ml PBS was mixed, using syringe-to-syringe mixing, with 50 mg of tetrafunctionally activated SE-PEG ("tetra SE-PEG", 10,000 MW, also obtained from Shearwater Polymers) in 0.5 ml PBS or trifunctionally activated SC-PEG ("tri SC-PEG", 5000 MW, also obtained from Shearwater Polymers) in 0.5 ml PBS.

Syringes containing each of the two mixtures were incubated at 37° C. for approximately 16 hours. Both compositions formed elastic gels. The gels were pushed out of the syringes and sliced into 5–6 mm thick disks having a diameter of 5 mm, for use in compression and swellability testing, as described below.

Figure 2:
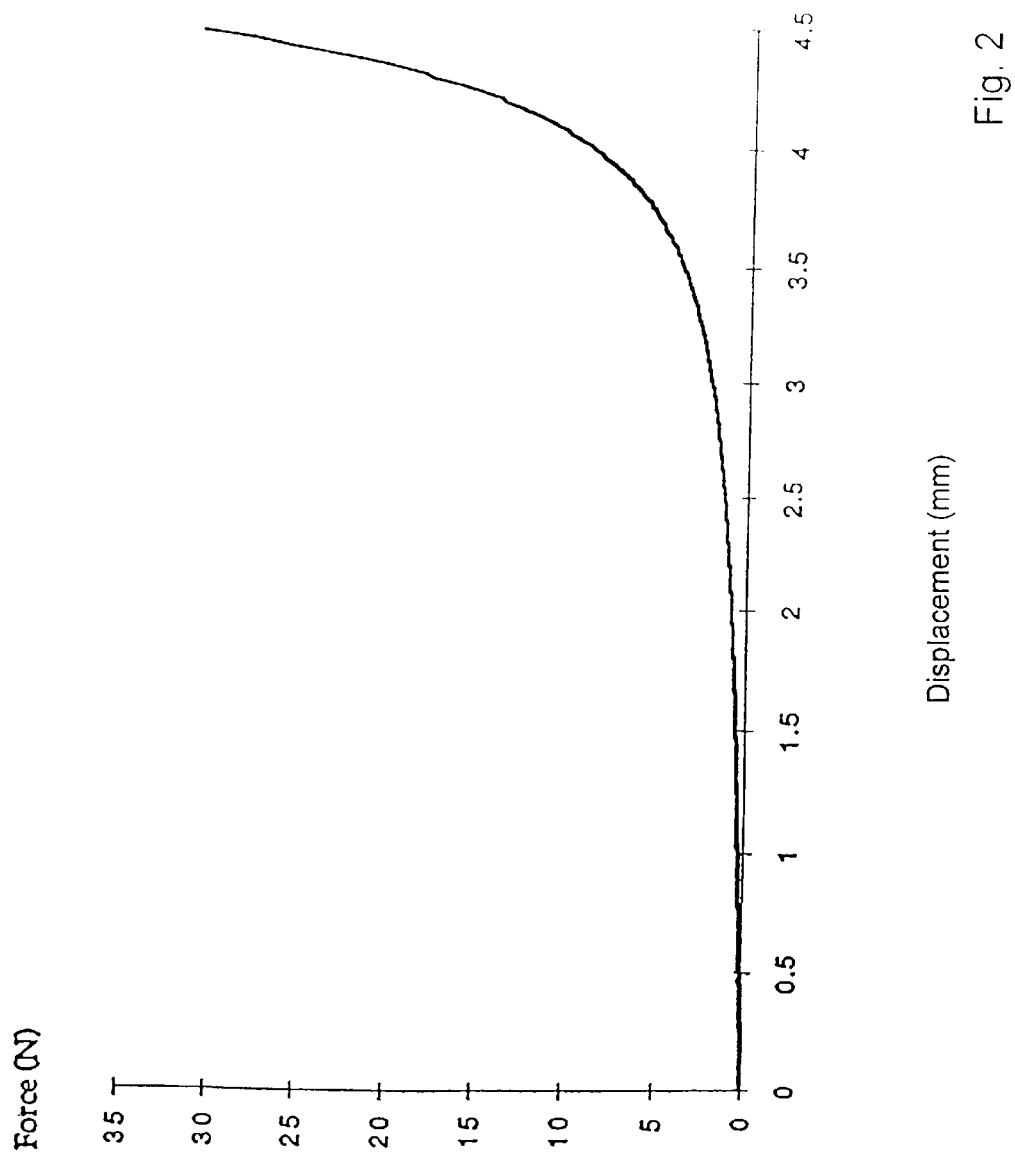
FIG. 2 shows compression force versus displacement for disks (approximate dimensions: 5 mm thick×5 mm diameter) of crosslinked polymer compositions comprising tetra-amino PEG (10,000 MW) crosslinked using trifunctionally activated SC-PEG (5,000 MW), measured using the Instron Universal Tester, Model 4202, at a compression rate of 2 mm per minute.

Compression force versus displacement for the two gels was measured in the Instron Universal Tester, Model 4202, at a compression rate of 2 mm per minute, using disks of the two gels prepared as described above. Compression force (in Newtons) versus gel displacement (in millimeters) is shown in FIGS. 1 and 2 for gels prepared using the tetra SE-PEG and tri SC-PEG, respectively.

Under compression forces as high as 30–35 Newtons, the gels did not break, but remained elastic.

Disks of each of the two gels, prepared as described above, were weighed and the dimensions (diameter and length) measured. The disks were then immersed in PBS and incubated at 37° C. After 3 days incubation, the disks were removed from the PBS, weighed, and measured. Results of swellability testing are shown in Table 2, below.

TABLE 2

Swellability Testing of Crosslinked Multi-amino PEG Compositions

| | Gel Weight (in grams) | | Dimensions (in mm) (diameter/thickness) | |
|---|---|---|---|---|
| Crosslinking Agent | Before Swelling | After Swelling | Before Swelling | After Swelling |
| Tetra SE-PEG | 0.116 | 0.310 | 5.0/5.0 | 7.1/8.1 |
| Tri SC-PEG | 0.131 | 0.287 | 5.0/6.0 | 6.4/8.5 |

As shown above, the gels swelled two to three times in weight, as well as swelling an average of about 50% in both diameter and thickness.

Example 4

Preparation of Crosslinked Poly(lysine) Compositions

Ten (10) milligrams of poly-t-lysine hydrobromide (8,000 MW, obtained from Peninsula Laboratories, Belmont, Calif.) in 0.1 ml phosphate buffer (0.2 M, pH=6.6) was mixed with 10 mg of tetrafunctionally activated SE-PEG (10,000 MW, obtained from Shearwater Polymers, Huntsville, Ala.) in 0.1 ml PBS. The composition formed a soft gel almost immediately.

Example 5

Preparation and Mechanical Testing of Crosslinked Multi-amino PEG Compositions Gels comprising tetra-amino PEG (10,000 MW, obtained from Shearwater Polymers, Huntsville, Ala.) and 1–4% (by weight) of tetrafunctionally activated SE-PEG ("tetra SE-PEG", 10,000 MW, also obtained from Shearwater Polymers) were prepared by mixing the tetra-amino PEG (at a concentration of 25 mg/ml in water) with the tetra SE-PEG (in PBS) in a petri dish. The resulting tetra-amino PEG/SE-PEG mixtures were incubated for 16 hours at 37° C.

The mixture containing 1% SE-PEG did not form a gel due to the low SE-PEG concentration. The mixture containing 2% SE-PEG formed a gel at some point during the 16-hour incubation period. The mixtures containing 3 and 4% SE-PEG formed gels within approximately 4–6 minutes of mixing. The gel containing 2% SE-PEG was readily extrudable through a 30-gauge needle; the gel containing 3% SE-PEG could be extruded through a 27-gauge needle.

The effect of elevated temperature on gel formation was evaluated. (Gels comprising tetra-amino PEG and 2.5% (by weight) tetra SE-PEG were prepared and incubated at temperatures of 37° C. and 4050° C. Elevated temperature was found to have a marked effect on gelation time: the tetra-amino PEG/SE-PEG mixture incubated at 37° C. formed a gel within approximately 20–25 minutes, whereas mixtures incubated at 40–50° C. formed gels within approximately 5 minutes. Both gels were extrudable through a 27-gauge needle.

The effect of pH on gel formation was evaluated. Gels comprising tetra-amino PEG and 2.5% (by weight) tetra SE-PEG were prepared as set forth in Table 3, below.

TABLE 3

Effect of pH on Gel Formation of Tetra-amino PEG/Tetra SE-PEG Formulations

| pH of Tetra-amino PEG | pH of Tetra SE-PEG | pH of Resulting Mixture | Gelation Time | Gelation Temp. |
|---|---|---|---|---|
| 10 | 4.1 | 6.9 | 10–15 minutes | 45° C. |
| 10 | 7.0 | 7.2 | <5 minutes | 45° C. |

Extrudability through a 27-gauge needle was evaluated for gels comprising tetra-amino PEG and 1–3% (by weight) tetra SE-PEG. The gels were contained within 1-cc syringes. The force required to depress the syringe plunger at a rate of 5 centimeters per minute was measured using the Instron Universal Tester, Model 4202. Results of extrusion testing are presented in Table 4, below.

TABLE 4

Extrusion of Tetra-amino PEG/Tetra SE-PEG Gels Through a 27-Gauge Needle

| Concentration of SE-PEG (by weight) | Extrusion Force (N) |
|---|---|
| 1.5–2% | 10–11 |
| 2–2.5% | 52 |
| 2.5–3% | 88 |

Extrusion forces of 100 N or less are considered acceptable for Manual injection without the aid of a syringe assist device.

Tensile strength (i.e., elasticity) of 3 mm thick gels comprising tetra-ammo PEG and 2.5, 5, and 10% (by weight) tetra SE-PEG was measured using the Instron Universal Tester, Model 4202. Gels of varying initial lengths were stretched at a rate of 10 millimeters per minute. Length of each gel, strain at failure (change in length as a percentage of the initial length), and force at failure are set forth in Table 5, below.

TABLE 5

Tensile Strength of Tetra-amino PEG/Tetra SE-PEG Gels

| SE-PEG Conc. (wt %) | Initial Length (cm) | Strain at Failure | Force at Failure (N) |
|---|---|---|---|
| 10 | 1.4 | 139% | 0.4 |
| 10 | 1.9 | 99% | 0.5 |
| 10 | 2.5 | 78% | 0.5 |
| 5 | 1.3 | 111% | 0.2 |
| 5 | 1.3 | 99% | 0.2 |
| 5 | 1.6 | 94% | 0.2 |
| 2.5 | 1.0 | 237% | <0.1 |
| 2.5 | 1.5 | 187% | <0.1 |
| 2.5 | 1.7 | 129% | <0.1 |

Gels containing 5 and 10% tetra SE-PEG approximately doubled in length prior to breaking. Gels containing 2.5% SE-PEG approximately tripled in length prior to breaking, but were considerably weaker (i.e., lower force at failure) than the more highly crosslinked gels.

Example 6

Effect of pH on Gel Formation of Tetra-amino PEG/Tetra SE-PEG Formulations

Gels comprising various concentrations of tetra-amino PEG and tetra SE-PEG at pH 6, 7, and 8 were prepared in petri dishes. Following mixing of the tetra-amino PEG and tetra SE-PEG, the dishes were tilted repeatedly; the gelation time was considered to be the point at which the formulation ceased to flow. The effect of pH on gelation time of the various tetra-amino PEG/tetra SE-PEG formulations at room temperature is shown in Table 6, below.

TABLE 6

Effect of pH on Gel Formation of Tetra-amino PEG/Tetra SE-PEG Formulations

| Tetra-amino PEG Conc. (mg/ml) | Tetra SE-PEG Conc. (mg/ml) | pH | Gelation Time |
|---|---|---|---|
| 20 | 20 | 6 | >90.0 min |
| 20 | 20 | 7 | 20.0 min |
| 20 | 20 | 8 | 1.4 min |
| 50 | 50 | 6 | 24.0 min |
| 50 | 50 | 7 | 3.5 min |
| 50 | 50 | 8 | 10.0 sec |
| 100 | 100 | 6 | 9.0 min |
| 100 | 100 | 7 | 47.0 sec |
| 100 | 100 | 8 | 10.0 sec |
| 200 | 200 | 6 | 2.0 min |
| 200 | 200 | 7 | 9.0 sec |
| 200 | 200 | 8 | 5.0 sec |

Time required for gel formation decreased with increasing pH and increasing tetra-amino PEG and tetra SE-PEG concentrations.

Example 7

Culturing of Cells in Crosslinked Multi-amino PEG Matrix

Thirty (30) milligrams of tetra-amino PEG (10,000 MW, obtained from Shearwater Polymers, Huntsville, Ala.) was dissolved in 0.6 ml PBS, then sterile filtered. Thirty (30) milligrams of tetrafunctionally activated SE-PEG ("tetra SE-PEG", 10,000 MW, also obtained from Shearwater Polymers) was dissolved in 0.6 ml of PBS, then sterile filtered.

The solutions of tetra-amino PEG and tetra SE-PEG were mixed together with a pellet containing human skin fibroblast ("HSF") cells (CRL #1885, passage 4, obtained from American Tissue Type Culture Collection, Rockville, Md.). Two hundred fifty (250) microliters of the resulting cell-containing tetra-amino PEG/tetra SE-PEG (PEG-PEG) solution was dispensed into each of two wells on a 48-well culture plate and allowed to gel for approximately 5 minutes at room temperature. One (1) milliter of Dulbecco Modified Eagle's Media (supplemented with 10% fetal bovine serum, L-glutamine, penicillin-streptomycin, and non-essential amino acids) was added to each of the two wells. The concentration of cells was approximately $3 \times 10^5$ cells per milliliter of tetra-amino PEG/tetra SE-PEG solution, or $7.5 \times 10^5$ cells per well.

To prepare a control, a pellet of HSF cells were suspended in 1.2 ml of complete media. Two hundred fifty (250) microliters of the control mixture was dispensed into each of three wells on the same 48-well culture plate as used above. Each well was estimated to contain approximately $7.5 \times 10^5$ cells. Each well was given fresh media every other day.

Initially, the cell-containing tetra-amino PEG/tetra SE-PEG gels were clear and the cells were found to be densely populated and spheroidal in morphology, indicating that there was little adhesion between the cells and the PEG/PEG gel (the cells would normally assume a flattened, spindle-shaped morphology when adhered to a substrate, such as to the treated plastic of the tissue culture plates). After three 3 days incubation at 37° C., the media in the wells containing the PEG/PEG gels was found to have lightened in color (Dulbecco Modified Eagle's Media is normally red in color), indicating a pH change in the media This indicated that the cells were alive and feeding. At 7 days incubation at 37° C., the cells were still spheroidal in morphology (indicating lack of adhesion to the gel) and the media had lightened even further, indicating that the cells were still viable and continued to feed.

On day 7, the contents of each well were placed in a 10% formalin solution for histological evaluation. According to histological evaluation, an estimated 75% of the cells in the wells containing the PEG/PEG gels appeared to be alive, but did not appear to be reproducing.

The results of the experiment indicate that HSF cells are viable in the tetra-amino PEG/tetra SE-PEG crosslinked gels, but did not seem to adhere to the gel and did not appear to reproduce while entrapped within the gel matrix. As described above, adherence or non-adherence of cells to a substrate material can influence the cells' morphology. In certain types of cells, cellular morphology can, in turn, influence certain cellular functions. Therefore, non-adherence of the cells to the PEG-PEG gel matrix may be an advantage in the delivery of particular cell types whose function is influenced by cell morphology. For example, the ability of cartilage cells to produce extracellular matrix materials is influenced by cellular morphology: when the cells are in the flattened, spindle-shaped configuration, the cells are in reproductive mode; when the cells are in the spheroidal configuration, reproduction stops, and the cells begin to produce extracellular matrix components.

Because the PEG-PEG gels are not readily degraded in vivo, the gels may be particularly useful in cell delivery applications where it is desirable that the cells remain entrapped within the matrix for extended periods of time.

What is claimed is:

1. A crosslinkable composition comprised of:
   (a) a first crosslinkable component having m nucleophilic groups, wherein $m \geq 2$;
   (b) a second crosslinkable component having n electrophilic groups capable of reaction with the m nucleophilic groups to form covalent bonds, wherein $n \geq 2$ and $m+n \geq 5$,
   wherein each of the first and second crosslinkable components is biocompatible, synthetic, and nonimmunogenic, and crosslinking of the composition results in a biocompatible, nonimmunogenic, crosslinked matrix.

2. The composition of claim 1, wherein the m nucleophilic groups are identical.

3. The composition of claim 1, wherein at least two of the m nucleophilic groups are different.

4. The composition of claim 1, wherein the n electrophilic groups are identical.

5. The composition of claim 2, wherein the n electrophilic groups are identical.

6. The composition of claim 3, wherein the n electrophilic groups are identical.

7. The composition of claim 1, wherein at least two of the n electrophilic groups are different.

8. The composition of claim 2, wherein at least two of the n electrophilic groups are different.

9. The composition of claim 3, wherein at least two of the n electrophilic groups are different.

10. The composition of claim 1, wherein the first and second crosslinkable components are non-naturally occurring, synthetic molecules.

11. The composition of claim 1, wherein the m nucleophilic groups are bound to the first crosslinkable component through linking groups.

12. The composition of claim 1, wherein the n electrophilic groups are bound to the second crosslinkable component through linking groups.

13. The composition of claim 1, wherein at least one of the first and second crosslinkable components is comprised of a hydrophilic polymer.

14. The composition of claim 1, wherein one of the first and second crosslinkable components is comprised of a hydrophobic polymer.

15. The composition of claim 1, wherein the m nucleophilic groups are primary amino groups.

16. The composition of claim 15, wherein the first crosslinkable component is $C_2$–$C_6$ hydrocarbyl substituted with amino groups.

17. The composition of claim 15, wherein the first crosslinkable component is a secondary or tertiary amine $NR_1R_2R_3$ wherein $R_1$ is hydrogen or an amino-substituted lower alkyl group, and $R_2$ and $R_3$ are amino-substituted lower alkyl groups.

18. The composition of claim 15, wherein the n electrophilic groups are selected from the group consisting of succinimidyl ester, sulfosuccinimidyl ester, maleimido, epoxy, isocyanato, thioisocyanato, and ethenesulfonyl.

19. The composition of claim 18, wherein the n electrophilic groups are selected from the group consisting of succinimidyl ester and sulfosuccinimidyl ester.

20. The composition of claim 1, wherein the m nucleophilic groups are sulfhydryl groups.

21. The composition of claim 20, wherein the n electrophilic groups are sulfhydryl-reactive groups selected so as to form a thioester, thioether, or disulfide linkage upon reaction with the sulfhydryl groups.

22. The composition of claim 1, wherein n=2.

23. The composition of claim 1, wherein m=2.

24. The composition of claim 1, further including an imaging agent.

25. The composition of claim 1, further comprising a therapeutically effective amount of a biologically active agent selected from the group consisting of enzymes, receptor antagonists, receptor agonists, hormones, growth factors, autogenous bone marrow, antibiotics, antimicrobial agents, antibodies, cells and genes.

26. The composition of claim 25, wherein the biologically active agent reacts with the first crosslinkable component, the second crosslinkable component, or both.

27. A crosslinkable system comprised of
    (a) a first crosslinkable component having m nucleophilic groups, wherein $m \geq 2$; and
    (b) a second crosslinkable component having n electrophilic groups capable of reaction with the m nucleophilic groups to form covalent bonds, wherein $n \geq 2$ and $m+n \geq 5$,
    wherein each crosslinkable component is biocompatible, synthetic, nonimmunogenic, and physically segregated from the other crosslinkable component, and crosslinking of the two components results in a biocompatible, nonimmunogenic, crosslinked matrix.

28. The crosslinkable system of claim 27, wherein the first crosslinkable component is in an aqueous solution.

29. The crosslinkable system of claim 27, wherein the first crosslinkable component is present in a molar excess relative to the second crosslinkable component.

30. The crosslinkable system of claim 27, wherein the second crosslinkable component is present in a molar excess relative to the first crosslinkable component.

* * * * *